United States Patent [19]

Effland et al.

[11] Patent Number: 5,039,811
[45] Date of Patent: Aug. 13, 1991

[54] PREPARATION OF N-(PYRIDINYL)-1H-INDOL-1-AMINES

[75] Inventors: Richard C. Effland; Joseph T. Klein, both of Bridgewater; Larry Davis, Sergeantsville; Gordon E. Olsen, Somerset, all of N.J.

[73] Assignee: Hoechst-Roussel Pharmaceuticals Inc., Somerville, N.J.

[21] Appl. No.: 571,473

[22] Filed: Aug. 23, 1990

Related U.S. Application Data

[60] Division of Ser. No. 405,156, Sep. 11, 1989, Pat. No. 4,970,218, which is a continuation-in-part of Ser. No. 171,102, Apr. 4, 1988, Pat. No. 4,880,822, which is a continuation-in-part of Ser. No. 42,079, Apr. 24, 1987, abandoned.

[51] Int. Cl.$^5$ ............................................. C07D 401/12
[52] U.S. Cl. ...................................................... 546/273
[58] Field of Search ........................................ 546/273

[56] References Cited

U.S. PATENT DOCUMENTS 4,536,505  8/1985  Browne .............................. 514/339

Primary Examiner—Jane T. Fan
Attorney, Agent, or Firm—Tatsuya Ikeda

[57] ABSTRACT

There are disclosed compounds of the formula,

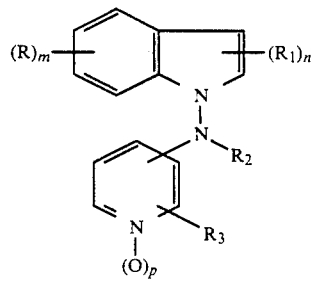

wherein m, n, p, R, $R_1$, $R_2$ and $R_3$ are as defined in the specification; which compounds are useful for enhancing memory and also as analgesic and antidepressant agents.

1 Claim, No Drawings

PREPARATION OF N-(PYRIDINYL)-1H-INDOL-1-AMINES

This is a division of a prior application Ser. No. 405,156, filed Sept. 11, 1989, now U.S. Pat. No. 4,970,218, which is a continuation-in-part of a prior application, Ser. No. 171,102, filed Apr. 4, 1988, now U.S. Pat. No. 4,880,822, which in turn is a continuation-in-part of a prior application, Ser. No. 042,079, filed Apr. 24, 1987, now abandoned.

The present invention relates to novel compounds of formula (I).

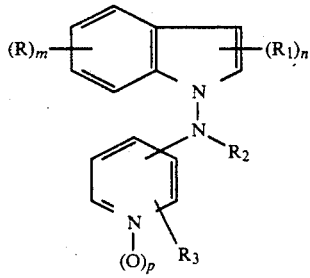

where
m is 1 or 2;
n is 1 or 2;
p is 0 or 1;
each R is independently hydrogen, halogen, loweralkyl, loweralkoxy, arylloweralkoxy, hydroxy, nitro, amino, loweralkylamino, loweralkylcarbonylamino, cyano, formyl, loweralkoxycarbonyl, loweralkylthio or loweralkoxycarbonylloweralkylthio;
each $R_1$ is independently hydrogen, loweralkyl, loweralkenyl, formyl, aldoxime, loweralkylcarbonyl, loweralkylcarbonyloxime, arylloweralkylcarbonyl, arylcarbonyl, halogen, arylloweralkenyl, arylloweralkyl, heteroarylloweralkenyl, heteroarylloweralkyl, cyanoloweralkenyl, cyanoloweralkyl, methoxyloweralkenyl, methoxyloweralkyl, aminoloweralkyl, loweralkylaminoloweralkyl, loweralkoxycarbonylloweralkenyl, loweralkoxycarbonylloweralkyl, cycloalkylloweralkenyl, cycloalkylloweralkyl, cyano, —CH(OH)$R_4$, —C(OH)$R_4R_5$, —CH$_2$OR$_5$, —CH=N$R_a$ or —CH$_2$NR$_a$R$_b$, the term heteroaryl signifying a group of the formula

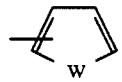

where W is O, S, NH or CH=N; $R_4$ being hydrogen, loweralkyl, aminoloweralkyl, arylloweralkyl, aryl or heteroaryl; $R_5$ being loweralkyl, loweralkylcarbonyl, arylloweralkyl or aryl; $R_a$ being loweralkyl, loweralkenyl, loweralkynyl, arylloweralkyl or —R$_6$—NR'R" where $R_6$ is loweralkylene, loweralkenylene or loweralkynylene and R' and R" are each independently loweralkyl or alternatively the group —NR'R" as a whole is 1-pyrrolidinyl, 1-piperidinyl, 4-morpholinyl, 4-loweralkyl-1-piperazinyl or 4-aryl-1-piperazinyl; and R$_b$ being hydrogen or loweralkylcarbonyl; $R_2$ is hydrogen, loweralkyl, haloloweralkyl, loweralkenyl, loweralkynyl, loweralkoxycarbonylloweralkyl, loweralkylaminocarbonylloweralkyl, aminocarbonylloweralkyl, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl or —R$_6$—NR'R"; and $R_3$ is hydrogen, nitro, amino, halogen, loweralkanoylamino, arylloweralkanoylamino, aroylamino, alkylamino, arylloweralkylamino, loweralkoxy, hydroxy or loweralkyl;
which compounds are useful for enhancing memory and also as analgesic and antidepressant agents; pharmaceutical compositions comprising an effective amount of such a compound and a method of treating a patient in need of memory enhancement, relief from pain or relief from depression which comprises administering such a compound to the patient.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen, $CF_3$, $NO_2$ or CN.

Unless otherwise stated or indicated, the term alkyl shall mean a saturated hydrocarbon group of 1 to 20 carbon atoms, the term alkenyl shall mean a hydrocarbon group of 1-20 carbon atoms having one or more carbon-carbon double bonds, and the term alkynyl shall mean a hydrocarbon group of 1-20 carbon atoms having one or more carbon-carbon triple bonds.

The term loweralkanoic acid shall mean a carboxylic acid in which the carboxyl group is attached to hydrogen or an alkyl group of from 1 to 5 carbon atoms.

The term loweralkanoyl shall mean a group obtained by removing a hydroxy group from the carboxyl group of a loweralkanoic acid, and thus it includes for instance formyl, acetyl and the like.

The term arylloweralkanoyl shall mean a loweralkanoyl group having an aryl substituent thereon, the term loweralkanoyl and aryl having the respective meanings defined above.

The term aroyl shall mean arylcarbonyl, an example being benzoyl.

The term arylloweralkyl shall mean a loweralkyl group having an aryl substituted thereon, the terms loweralkyl and aryl having the respective meanings defined above.

The terms alkanoyl, alkenoyl and alkynoyl shall mean groups obtained by removing a hydroxy group from the carboxyl group of alkanoic acid, alkenoic acid and alkynoic acid, respectively. Thus, for instance, linoleyl group derived from linoleic acid is an example of the term alkenoyl as defined above.

The term acyl shall mean loweralkanoyl or arylloweralkanoyl as defined above.

The term cycloalkyl in each occurrence shall mean an alicyclic group of 3 to 7 ring carbons.

The term heteroaryl in each occurrence shall mean a group of the formula

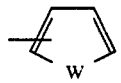

where W is O, S, NH or CH=N.

The compounds of formula (I) of this invention can be synthesized by following or combining one or more of the steps described below, not necessarily in the order presented. For the sake of simplification, the description of synthetic schemes is presented below for compounds in which m=n=1, but it will be apparent that other compounds in which m and/or n is 2 can be prepared by utilizing the synthetic schemes and making necessary modifications. Throughout the description of the synthetic steps, the definitions of R, $R_1$ through $R_6$, R', R'', m, n and p are as given above unless otherwise stated or indicated, and other nomenclatures appearing below shall have the same meanings defined in their respective first appearances unless otherwise stated or indicated.

STEP A

A compound of formula (II) where $R_7$ is H, halogen, loweralkyl, loweralkoxy, arylloweralkoxy, nitro, cyano, formyl, loweralkylthio or loweralkoxycarbonyl-loweralkylthio, $R_8$ is H, loweralkyl, cyanoloweralkyl, halogen or cyano and $R_9$ is H or loweralkyl is reacted with a compound of formula (III) where X is chlorine or fluorine and $R_{10}$ is H, $NO_2$, halogen, loweralkyl or loweralkoxy to afford a compound of formula (IV).

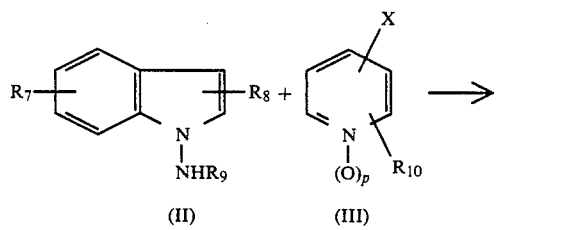

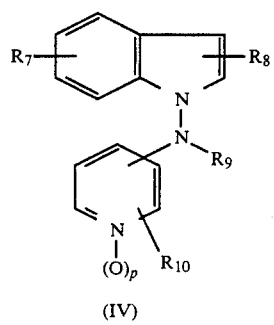

Said reaction is typically conducted in an ethereal solvent such as bis(2-methoxyethyl)ether, diethyl ether, dimethoxy ether, dioxane or tetrahydrofuran or polar aprotic solvent such as dimethylformamide, dimethylacetamide, N-methyl-2-pyrrolidone, hexamethylphosphoramide or dimethylsulfoxide or protic solvent such as ethanol or isopropanol at a temperature of between about 20° C. and 150° C.

STEP B

A compound of formula IVa obtained from STEP A is treated with a strong base such as sodium hydride or potassium hydride in a suitable solvent such as polar aprotic solvent including dimethylformamide, dimethylsulfoxide and ethereal solvents or aromatic hydrocarbon at a temperature of between about −10° and 50°, preferably 0°–25° to form the anion of IVa, which is reacted with a chloride or bromide compound of the formula $R_{11}$—Cl or $R_{11}$—Br, where $R_{11}$ is loweralkyl, haloloweralkyl, loweralkoxycarbonylloweralkyl, loweralkenyl, loweralkynyl, arylloweralkyl, loweralkoxycarbonyl, arylloweralkoxycarbonyl or aryloxycarbonyl at a temperature of between about −10° and 80°, preferably between 0° and 25° to obtain a compound of formula V.

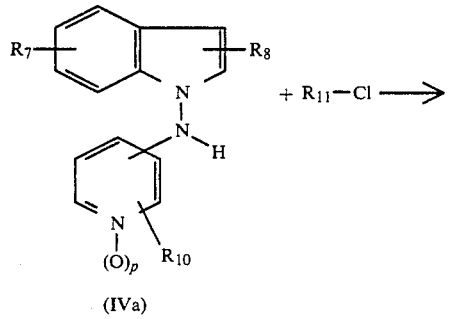

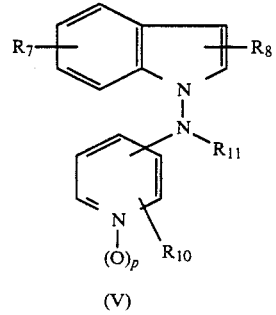

STEP C

The anion of compound IVa prepared as in STEP B is reacted with fluoro-nitrobenzene, cyano-fluorobenzene or fluoro-trifluoromethylbenzene of the formula

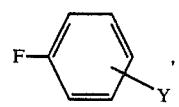

where Y is nitro, cyano or trifluoromethyl to afford a compound of formula VI below. Said reaction is conducted in substantially the same manner as in STEP B.

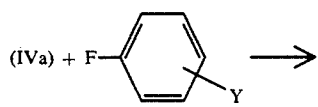

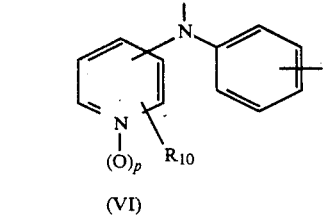

(VI)

STEP D

Compound IVa is reacted with a loweralkyl isocyanate, arylloweralkyl isocyanate or aryl isocyanate of the formula $R_{12}NCO$ where $R_{12}$ is loweralkyl, arylloweralkyl or aryl to afford a compound of formula VII.

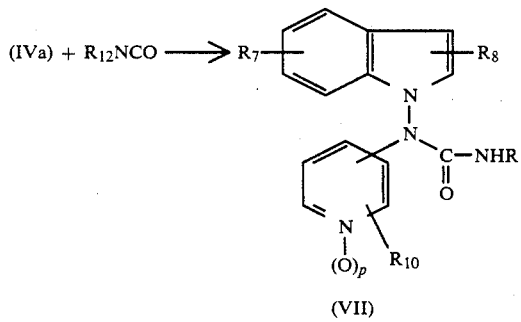

(VII)

Said reaction is typically conducted in a suitable solvent such as aromatic hydrocarbon including benzene, toluene and the like, halogenated hydrocarbon or ethereal solvent at a temperature of about 0°–80°, preferably 30°–60° C.

STEP E

Compound IVa is reacted with an alkanoyl chloride, arylloweralkanoyl chloride, aroyl chloride, alkenoyl chloride or alkynoyl chloride of formula (VIII) where $R_{13}$ is alkyl, arylloweralkyl, aryl, alkenyl or alkynyl to afford a compound of formula (IX). Said reaction is typically conducted in substantially the same manner as in STEP D.

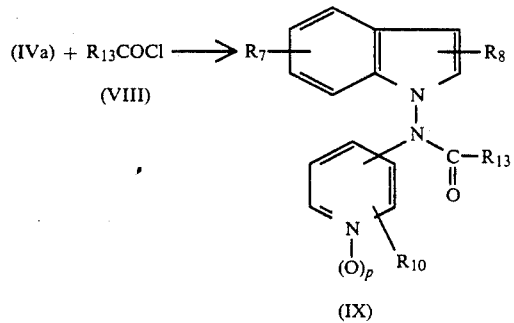

(IX)

Where the compound $R_{13}COCl$ is not commercially available, it is prepared from the corresponding carboxylic acid $R_{13}COOH$ and thionyl chloride in a suitable solvent, for instance, in benzene at the reflux temperature.

STEP F

As an alternative to STEP A or B, a compound of formula (IVb) where $R_{14}$ is loweralkyl can be prepared by reacting compound IVa with a strong base such as sodium hydride or potassium hydride and then reacting the product with a diloweralkyl sulfate of the formula $(R_{14})_2SO_4$. Said two steps are conducted under substantially the same conditions as used in STEP B.

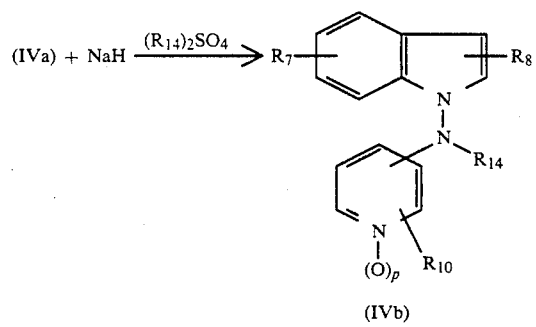

(IVb)

STEP G

A compound of formula Va obtained in STEP B is subjected to Mannich reaction with formaldehyde and a secondary amine of the formula HNR′R″, where R′ and R″ are independently loweralkyl or —NR′R″ taken together is 1-pyrrolidinyl, 1-piperidinyl, 4-morpholinyl, 4-loweralkyl-1-piperazinyl or 4-aryl-1-piperazinyl to afford a compound of formula X.

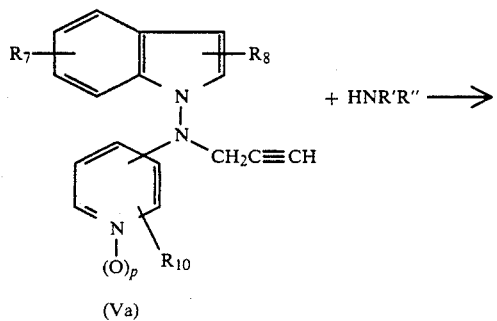

(Va)

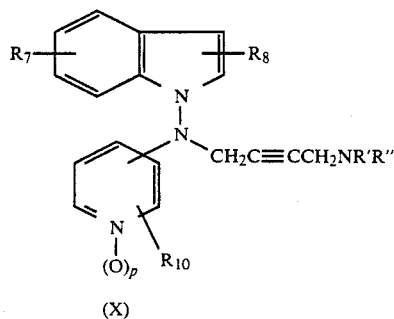

(X)

The above reaction can be conducted under conditions usually used in the art for carrying out Mannich reactions. Typically, it is conducted by preparing a mixture of compound Va, paraformaldehyde, HNR'R", cuprous chloride (used as a catalyst) and a suitable medium including ethereal solvents such as dioxane, and heating the mixture at 25°-100°.

STEP H

Compound X is catalytically hydrogenated to afford a compound of formula XI or XII by making a suitable selection of reaction conditions in a manner known to the art.

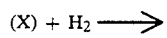

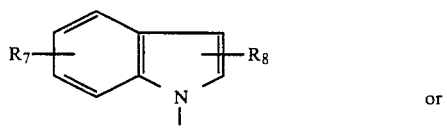

(XI)

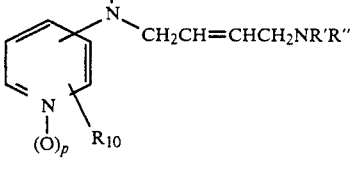

(XII)

STEP I

As an alternative to the foregoing steps, a compound of formula XIV where $R_{15}$ is loweralkyl, loweralkoxycarbonylloweralkyl, arylloweralkyl, aryl, loweralkoxycarbonyl, arylloweralkoxycarbonyl, aryloxycarbonyl, alkanoyl, arylloweralkanoyl or aroyl can be prepared by reacting a compound of formula XIII with a suitable chlorinating agent such as sulfuryl chloride ($SO_2Cl_2$) in a manner known in the art.

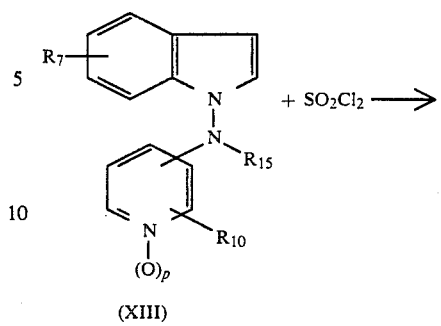

(XIII)

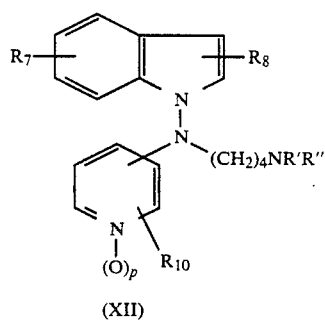

(XIV)

STEP J

A compound of formula (XV) where $R_{16}$ is loweralkyl, loweralkoxycarbonyl, alkanoyl, alkenoyl, alkynoyl, arylloweralkanoyl or aroyl, and $R_{17}$ is H, $NO_2$, halogen or loweralkyl which is prepared by use of one or more of the reaction steps described in this specification is reacted with phosphorus oxychloride and dimethylformamide to afford a compound of formula (XVI).

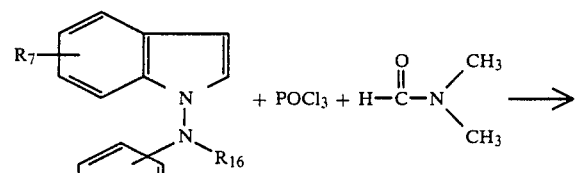

(XV)

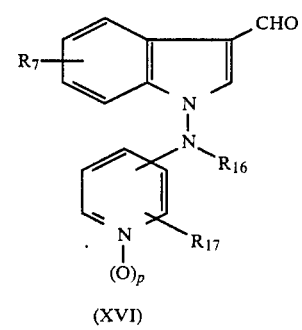

(XVI)

Said reaction can be conducted under conditions usually used for carrying out Vilsmeier reactions. Typically, it is conducted in a suitable solvent such as halogenated hydrocarbon at a temperature of about 20°–100°.

Where the positional isomer of compound XVI in which the formyl group is at the 2-position of the indole ring is desired, compound XV is reacted with secondary butyllithium and the resultant lithio compound reacted with N-formyl-N-methyl-aniline in a manner known in the art.

STEP K

Compound XV is reacted with a loweralkanoyl chloride, arylloweralkanoyl chloride or aroyl chloride of formula $R_{12}COCl$ in the presence of zinc chloride to afford a compound of formula (XVII). Said reaction is typically conducted in a suitable solvent such as halogenated hydrocarbon at a temperature of about 20°–100° C.

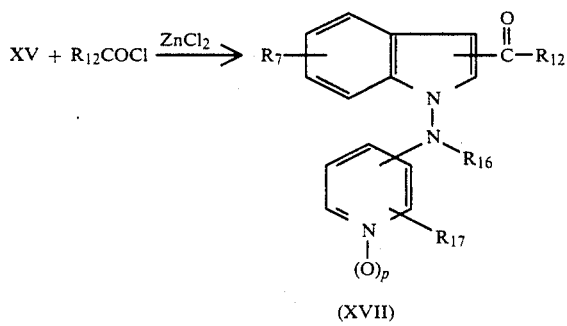

(XVII)

Where the positional isomer of compound XVII in which the group —C(O)$R_{12}$ is at the 2-position of the indole ring is desired, compound XV is reacted with secondary butyllithium and the resultant lithio compound reacted with $R_{12}COCl$ in a manner known to the art.

STEP L

A compound of formula XVIII below where $R_{18}$ is H, halogen or loweralkyl is reduced to a compound of formula XIX below with NaBH$_4$, LiAlH$_4$ or borane complexes.

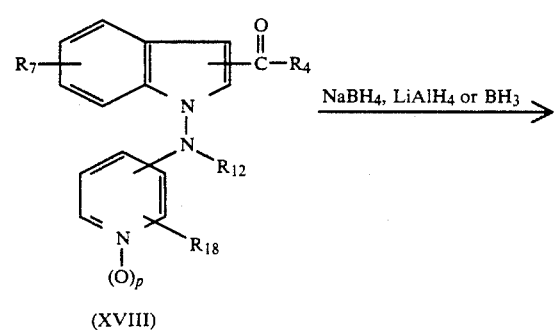

(XVIII)

(XIX)

When NaBH$_4$ is used, said reduction is conducted typically in a lower aliphatic alcohol such as isopropanol or ethanol or loweralkanoic acid at a temperature of about 0°–80°. After the reaction, water is added to the reaction mixture. When LiAlH$_4$ is used, said reduction is conducted typically in an ethereal solvent such as tetrahydrofuran or ether at a temperature of about 0°–80°. When borane complexes are used, the reaction temperature is typically 0°–80° C.

STEP M

Compound XVIII is reacted with a Grignard reagent of the formula $R_5MgBr$ (where $R_5$ is not loweralkylcarbonyl) and the product is thereafter hydrolyzed to afford a compound of formula XX below.

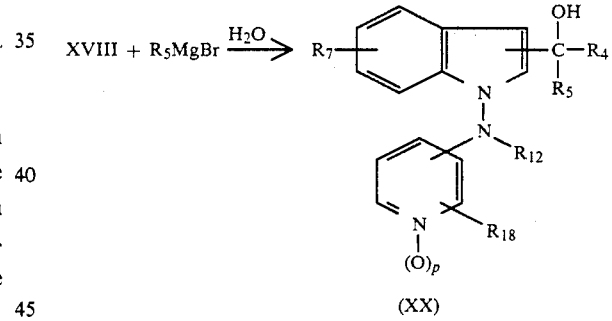

(XX)

STEP N

A compound of formula XXI which is prepared by use of one or more of the reaction steps described in this specification is catalytically hydrogenated with hydrogen gas and a suitable catalyst such as palladium on carbon to afford a compound of formula (XXII).

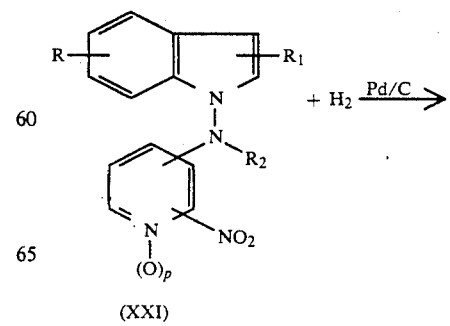

(XXI)

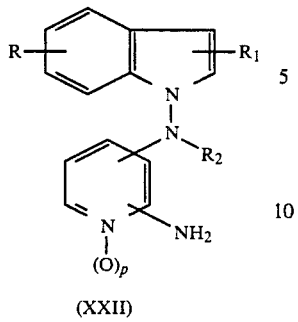

(XXII)

Said catalytic hydrogenation is typically conducted in a suitable solvent such as loweralkanol or loweralkyl ester of loweralkanoic acid at a temperature of 20°–50° C.

STEP O

As an alternative to the foregoing steps, compound IVa can be prepared by hydrolyzing a carbamate compound of formula Vb. (Needless to say, the purpose of this STEP is not to reverse aforementioned STEP B in order to regain the starting compound of STEP B. This STEP can be useful, for instance, for the purpose of converting $R_8$ in formula IVa from hydrogen to 3-chloro. Thus, for this purpose, one can first convert the amino hydrogen in formula IVa to ethoxycarbonyl by use of STEP B or similar to STEP E and then introduce a chlorine atom into the 3-position of the indole ring by use of STEP I and thereafter hydrolyze the resultant product by use of this STEP, instead of conducting the chlorination reaction directly with compound IVa. Similarly, this STEP can also be useful for introducing the group $-COR_{12}$ into the indole ring according to STEP K above or the group $-CHO$ according to STEP J when $R_2$ is hydrogen.

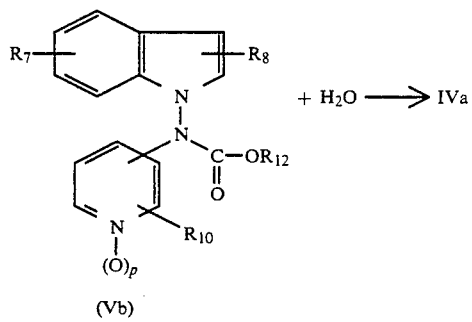

(Vb)

Said hydrolysis is conducted typically by stirring a mixture comprising compound Vb, an alkali such as NaOH and a suitable medium such as ethanol plus water at a temperature of about 70°–100° C.

STEP P

Compound XXII is reacted with phenyl formate to afford a compound of formula (XXIII)

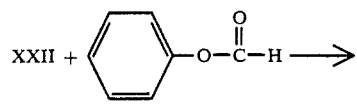

(XXIII)

Typically said reaction is conducted by stirring a solution of compound XXII in excess phenyl formate at a temperature of about 20°–50° C. The same reaction can also be conducted with loweralkyl formate under substantially the same conditions.

STEP Q

Compound XXII is reacted with an acyl chloride of the formula $R_{12}COCl$ or acid anhydride of the formula $R_{12}CO-O-COR_{12}$ to afford a compound of formula XXIV.

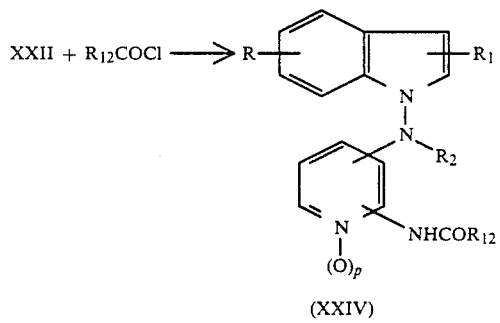

(XXIV)

Said reaction is conducted under substantially the same conditions as used in STEP E.

STEP R

As an alternative to the foregoing steps, a compound of formula XXV where $R_1$ is H or loweralkyl, and $R_2$ is loweralkyl, arylloweralkyl, phenyl, nitrophenyl, or trifluoromethylphenyl, can be prepared by reacting a compound of formula (IVc) with a loweralkyl lithium of the formula $R_{19}Li$ where $R_{19}$ is loweralkyl.

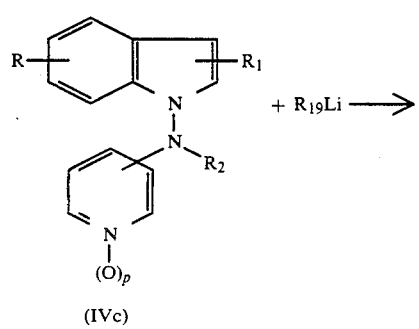

(IVc)

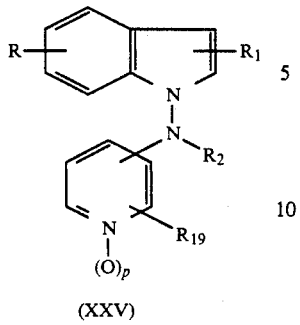

(XXV)

Said reaction is usually conducted in a suitable solvent such as ethereal solvent, preferably tetrahydrofuran at a temperature of between about −10° and 50° C.

STEP S

A compound of formula XIXa below is reacted with a strong base such as sodium hydride or potassium hydride and the resultant alkoxide anion is reacted with a halide of the formula $R_5X$ to afford an ether of formula XXVI below. Said two-step procedure is conducted in substantially the same manner as in STEP B above.

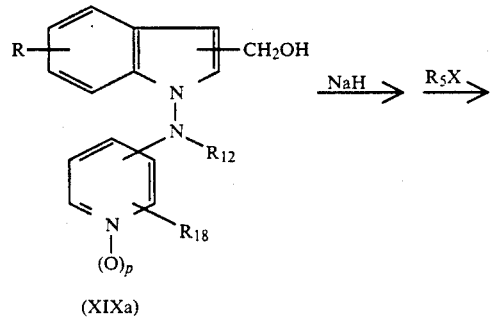

(XIXa)

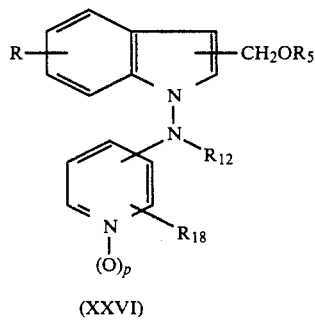

(XXVI)

STEP T

Compound XVI is subjected to Wittig reaction with an ylide of the formula $(C_6H_5)_3P=CR_{20}R_{21}$ to afford a compound of formula XXVII where $R_{20}$ and $R_{21}$ are each independently hydrogen, loweralkyl, aryl, arylloweralkyl, heteroaryl, heteroarylloweralkyl, cyano, methoxy, loweralkoxycarbonyl or together form a cycloalkylidene.

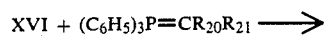

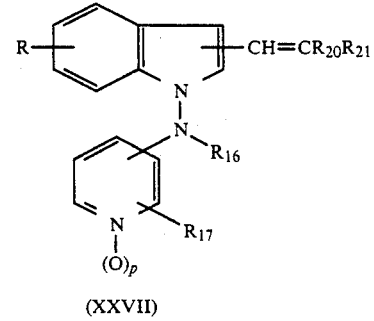

(XXVII)

The above reaction can be conducted under conditions usually used for carrying out Wittig reactions. Thus, the ylide is prepared in a routine manner by first preparing a phosphonium salt from a bromide of the formula $BrCHR_{20}R_{21}$ and triphenylphosphine and thereafter reacting the phosphonium salt with a suitable base such as sodium hydride, potassium tert-butoxide or n-butyllithium in a suitable solvent such as anhydrous ethereal solvent. Thereafter a solution of compound XVI in a suitable solvent such as anhydrous ether is added to the freshly prepared ylide solution and the mixture is stirred at a temperature of between about −10° C. and 80° C.

It will be apparent that by making a suitable selection of the groups $R_{20}$ and $R_{21}$ and/or conducting Wittig reaction more than once if necessary, one can obtain compounds of formula XXVIII where the group $R_{22}$ is loweralkenyl, arylloweralkenyl, heteroarylloweralkenyl, cyanoloweralkenyl, methoxyloweralkenyl, loweralkoxycarbonylloweralkenyl, or cycloalkylloweralkenyl.

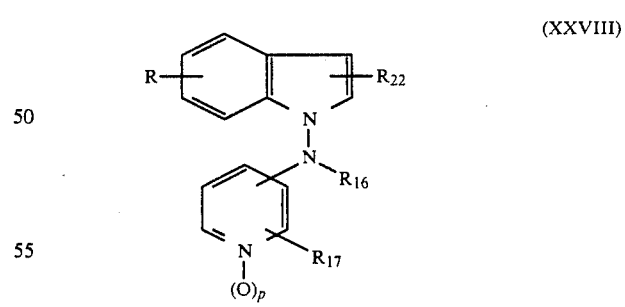

(XXVIII)

STEP U

Compound XXVIII is catalytically hydrogenated in a suitable manner known to the art to afford a compound of formula XXIX where $R_{23}$ is loweralkyl, arylloweralkyl, heteroarylloweralkyl, cyanoloweralkyl, methoxyloweralkyl, loweralkoxycarbonylloweralkyl or cycloalkylloweralkyl.

XXVIII + H₂ ⟶ 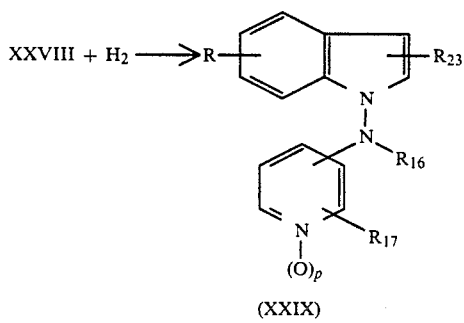

(XXIX)

STEP V

Substantially the same hydrogenation technique as described in STEP N or U can be used to hydrogenate a compound of formula XXX below to afford a compound of formula XXXI below.

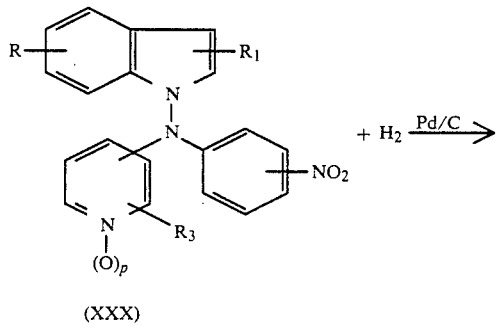

(XXX)

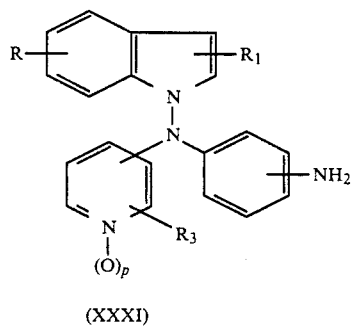

(XXXI)

STEP W

Substantially the same reaction technique as described in STEP P can be used to convert compound XXXI to a compound of formula XXXII below.

(XXXI) + 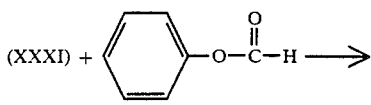 ⟶

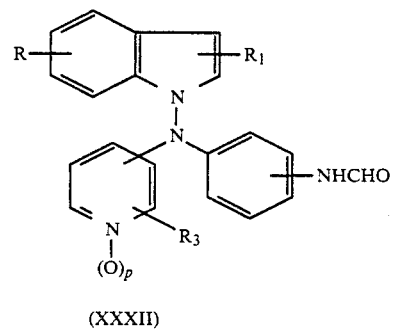

(XXXII)

STEP X

Substantially the same reaction technique as described in STEP Q can be used to convert compound XXXI to a compound of formula XXXIII below.

(XXXI) + R₁₂COCl ⟶ 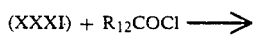

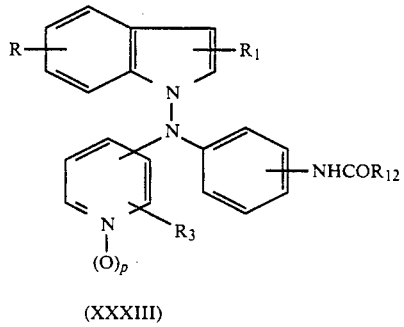

(XXXIII)

STEP Y

As an alternative to the foregoing steps, introduction of a cyano group into the 2- or 3-position of the indole ring can be accomplished by using, as a starting compound, the formyl compound of formula XXXIV and converting the formyl group into a cyano group. For this purpose, compound XXXIV is first reacted with hydroxylamine in a routine manner to obtain the corresponding oxime and thereafter the oxime is reacted with benzenesulfonyl chloride to obtain a nitrile compound of formula XXXV. The second step is typically conducted in a suitable solvent such as ethereal solvent by warming the reaction mixture at 60°–100° C.

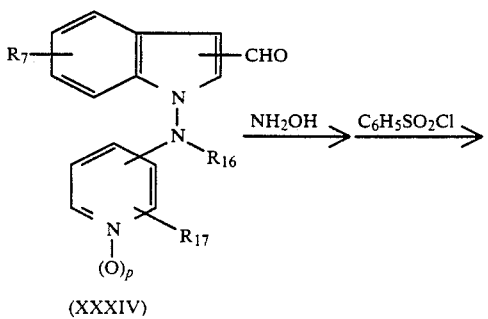

(XXXIV)

-continued

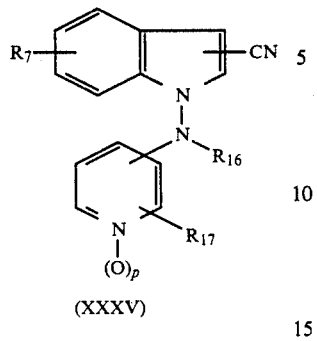

(XXXV)

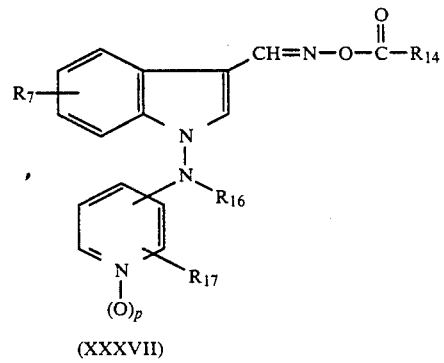

(XXXVII)

STEP Z

For the purpose of preparing a compound of formula I where $R_2$ is aminocarbonylloweralkyl, a compound of formula I where $R_2$ is loweralkoxycarbonylloweralkyl (preferably ethoxycarbonylloweralkyl) is reacted with ammonia in a manner known to the art.

STEP AA

Compound XVI is allowed to react with hydroxylamine hydrochloride to afford a compound of formula XXXVI.

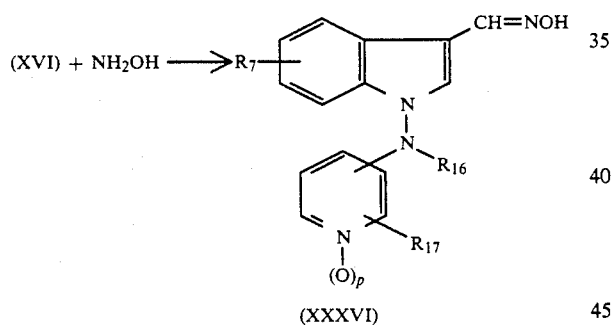

(XXXVI)

This reaction is typically conducted in a suitable solvent such as pyridine at a temperature of about 0° to 80° C.

STEP BB

Compound XXXVI is allowed to react with a loweralkanoyl chloride or bromide of the formula,

in a routine manner known to the art to afford a compound of Formula XXXVII.

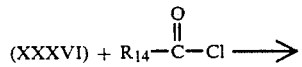

STEP CC

Compound XXXVI is reduced to a compound of Formula XXXVIII. It is preferable to conduct this reduction with the aid of Raney alloy (50:50 Al/Ni alloy). Thus, typically to a mixture comprising Compound XXXVI, ethanol and Raney alloy is added an aqueous solution of NaOH and a reflux condition is maintained for a suitable length of time such as one hour.

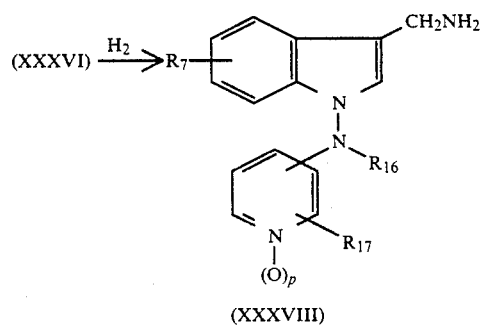

(XXXVIII)

STEP DD

A compound of Formula XXXIX, which is obtained from a compound of Formula IIa by utilizing one or more of the foregoing synthetic steps, is reduced to the corresponding aminoethyl compound of Formula XL in a routine manner known to the art.

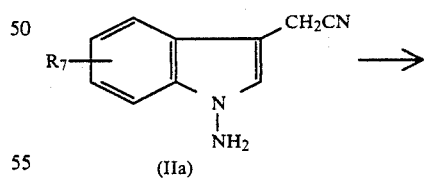

(IIa)

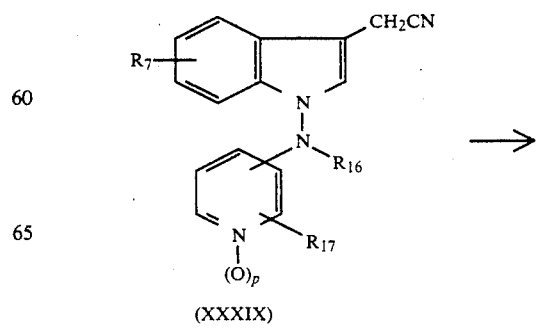

(XXXIX)

-continued

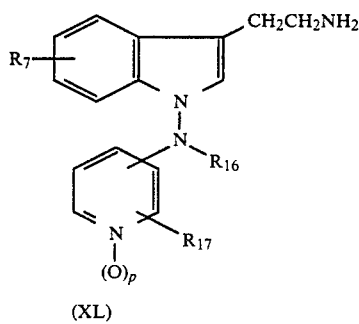

(XL)

STEP EE

A compound of Formula XLI where —R$_{24}$CN is a cyano group (R$_{24}$ being null) or a cyanoloweralkyl group, (the former type of compound is obtained, for instance, from STEP Y, and the latter type of compound is obtained from STEP U) is reduced compound is obtained from STEP U) is reduced to the corresponding aminoloweralkyl compound of Formula XLII in a routine manner known to the art.

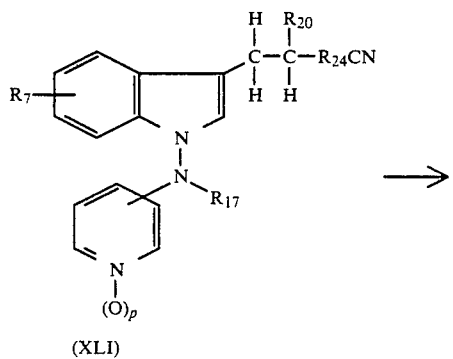

(XLI)

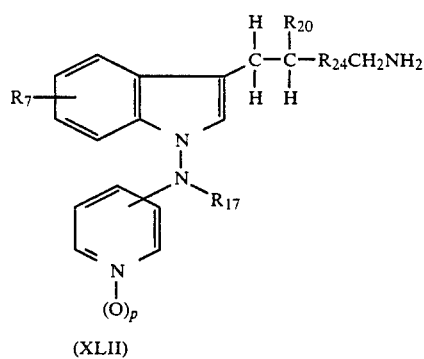

(XLII)

STEP FF

A compound of Formula XLIII where —R$_{25}$NH$_2$ constitutes an aminoloweralkyl group which is obtained from STEP CC, STEP DD or STEP EE is first allowed to react with a loweralkanoyl chloride or bromide of the formula,

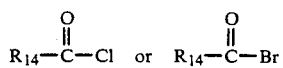

in a routine manner known to the art and the resultant acylation product is reduced in a routine manner known to the art to afford a corresponding loweralkylamino-loweralkyl compound of Formula XLIV.

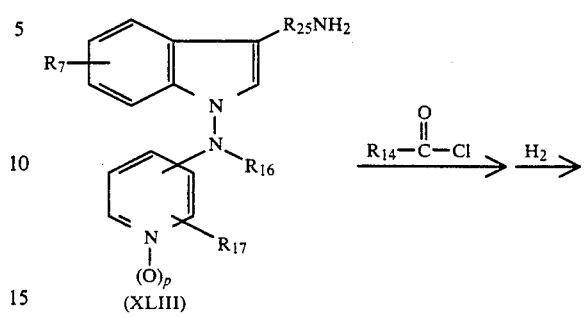

(XLIII)

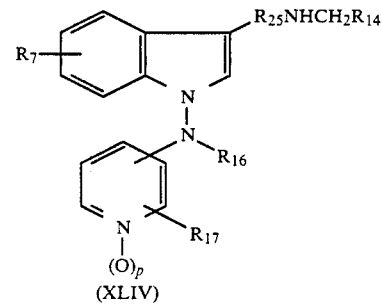

(XLIV)

STEP GG

Compound XVI is allowed to react with a compound of Formula XLV and the resultant product is reduced with LiAlH$_4$ to afford a compound of Formula XLVI.

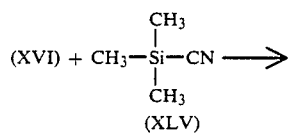

(XLV)

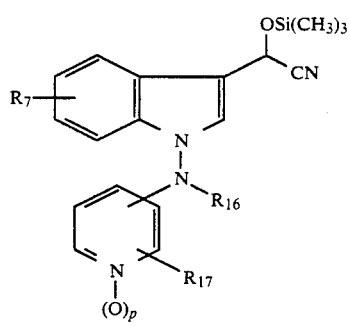

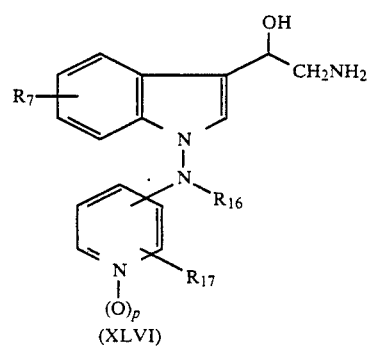

(XLVI)

The first reaction mentioned above is conducted in the presence of a small amount of ZnI₂ and a suitable solvent such as dichloroethane at a temperature of about 0° to 85° C. The second reaction is typically conducted in a suitable solvent such as THF at a temperature of 0° to 65° C.

STEP HH

Compound XVI is allowed to react with a primary amine of the formula H₂NR$_a$, where R$_a$ is as defined earlier except that it is not hydrogen to afford a corresponding Schiff base of Formula XLVII.

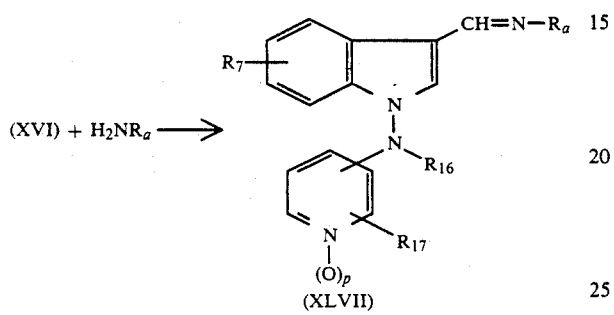

STEP II

Compound XLVII is reduced with NaBH₄ to afford a compound of Formula XLVIII. This reduction is typically conducted in a suitable medium such as isopropanol at a temperature of about 0° to 80° C.

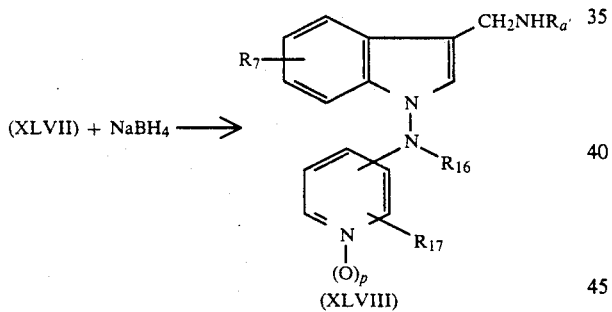

STEP JJ

Compound XIX is oxidized with the aid of pyridinium dichromate to afford compound XVIII. Said oxidation is typically conducted in a suitable solvent such as halogenated hydrocarbon or preferably polar aprotic solvent such as dimethylformamide, dimethylacetamide, N-methyl-2-pyrrolidone, hexamethylphosphoramide or dimethylsulfoxide at a temperature of between about 0° C. and 100° C.

STEP KK

Compound XLVIII is allowed to react with an acyl chloride of the formula R₁₄COCl or with an acid anhydride of the formula (R₁₄CO)₂O, where R₁₄ is loweralkyl, in a routine manner known to the art to afford a compound of formula IL.

(XLVIII) + R₁₄COCl or (R₁₄CO)₂O ⟶

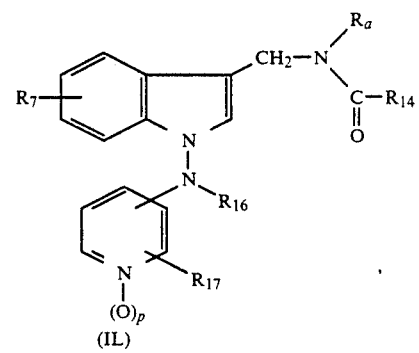

STEP LL

A compound of Formula L obtained from one of the foregoing STEPS is subjected to a cleavage reaction in a routine manner known to the art to afford a corresponding hydroxy compound of Formula LI.

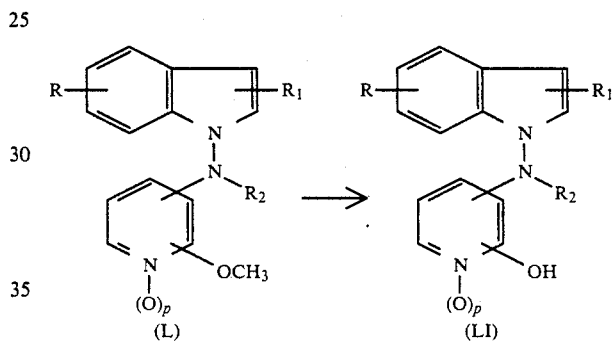

The compounds of formula I of the invention are useful in the treatment of various memory dysfunctions characterized by decreased cholinergic function, such as Alzheimer's disease.

This utility is demonstrated by the ability of these compounds to restore cholinergically deficient memory in the Dark Avoidance Assay, where they are generally active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is countered by an active test compound, resulting in a greater interval before re-entry into the dark compartment.

The results for active compound are expressed as the percent of a group of animals in which the effect of scopolamine is countered, as manifested by an increased interval between being placed in the test chamber and re-entering the dark compartment.

The results of some of the compounds of this invention are presented in Table 1 along with the result of physostigmine.

TABLE 1

| Compound | Dose mg/kg Body Weight s.c. | % of Animals With Scopolamine Induced Memory Deficit Reversed |
|---|---|---|
| Physostigmine (namely, (3aS-cis)-1,2,3,3a,8,8a-hexahydro-1,3a,8-trimethyl-pyrrolo[2,3-b]indol-5-ol, methyl carbamate) | 0.31 | 20% |
| N-Methyl-N-(4-pyridinyl)-1H-indol-1-amine maleate | 0.04 | 53% |
| N-(4-Pyridinyl)-1H-indol-1-amine maleate | 0.31 | 33% |
| N-Propyl-N-(4-pyridinyl)-1H-indol-1-amine maleate | 0.08 | 27% |
| N-Ethyl-N-(4-pyridinyl)-1H-indol-1-amine maleate | 0.63 | 33% |
| N-(3-Fluoro-4-pyridinyl)-N-propyl-3-methyl-1H-indol-1-amine hydrochloride | 0.31 | 33% |
| 3-Methyl-N-propyl-N-(4-pyridinyl)-1H-indol-1-amine maleate | 0.31 | 27% |

Additionally, some of the compounds of this invention exhibit antidepressant activities, which activities being particularly helpful for patients suffering from Alzheimer's disease. The antidepressant activities were evaluated in this invention on the basis of prevention of Tetrabenazine-induced ptosis in mice. The test method and results are described below.

Prevention of Tetrabenazine-Induced Ptosis in Mice

Tetrabenazine (TBZ) induces behavioral depression with concomitant ptosis in mice similar to reserpine. Antidepressant compounds, both monoamineoxidase inhibitors and tricyclics, are known to prevent or antagonize these effects and the degree of antagonism correlates with clinical efficacy. The prevention of TBZ-induced ptosis in mice is used as a preliminary screen for possible antidepressant activity. The method used in this invention is as follows:

Male mice weighing 20 to 30 grams are used in test groups of five subjects. All compounds are dissolved or suspended with a suitable surfactant in distilled water and administered in volumes of 10 ml/kg of body weight. TBZ solution is made from the methanesulfonate salt and the concentration is adjusted to enable administration of 60 mg/kg of base by intraperitoneal (i.p.) injection.

The pretreatment time is measured from the time of dosing to observation. Therefore, when a 30-minute pretreat is utilized, drug and TBZ are given simultaneously. A control group received solvent and TBZ at intervals identical to drug group. For a primary screen, the drug is administered i.p. and a group size of five is utilized. Eight animals/group are used for a dose range.

Thirty minutes after TBZ, the subjects are placed in individual plastic containers (10.5×8×6 inches) in the presence of white noise and one minute after the transfer, they are scored for ptosis on the following scale: Eyes closed=4, eyes ¾ closed=3, eyes ½ closed=2, eyes ¼ closed=1, eyes open=0. The total score for each group of five in a primary screen will, therefore, be from 0 to 20 and these scores are used as indications of drug activity.

The vehicle control group score is used as a determinant of the validity of each test. If the control score is less than 17, the results are discarded and the test repeated. The calculation of percent inhibition of ptosis is:

$$\frac{(\text{Control Score} - \text{Drug Score})}{\text{Control Score}} \times 100\%$$

For $ED_{50}$ estimation, four or five doses are administered in order to bracket the estimated value and only vehicle control scores of 27 to 32 are accepted to assure the accuracy of the $ED_{50}$ estimation.

Linear regression analysis is used to estimate $ED_{50}$ values and 95% confidence intervals.

The results of some of the compounds of this invention are shown in Table 2 along with a result for desipramine (prior art compound).

TABLE 2

| Compound | $Ed_{50}$ (mg/kg) |
|---|---|
| N-methyl-N-(4-pyridinyl)-1H-indol-1-amine maleate | 3.3 (p.o.) |
| N-(4-pyridinyl)-1H-indol-1-amine maleate | 3.3 (p.o.) |
| N-propyl-N-(4-pyridinyl)-1H-indol-1-amine maleate | 5.1 (p.o.) |
| N-ethyl-N-(4-pyridinyl)-1H-indol-1-amine maleate | 5.6 (p.o.) |
| N-methyl-N-(4-pyridinyl)-1H-indol-1-amine-3-carboxaldehyde maleate | 9.7 (p.o.) |
| N-ethyl-N-(4-pyridinyl)-1H-indol-1-amine-3-carboxaldehyde maleate | 11.9 (p.o.) |
| 5-methoxy-N-propyl-N-(4-pyridinyl)-1H-indol-1-amine maleate | 29.8 (p.o.) |
| 3-Methyl-N-(4-pyridinyl)-1H-indol-1-amine oxalate | 1.0 (i.p.) |
| 3-Methyl-N-propyl-N-(4-pyridinyl)-1H-indol-1-amine maleate | 1.8 (i.p.) |
| N-(2-Propen-1-yl)-N-(4-pyridinyl)-1H-indol-1-amine maleate (Prior Art Compound) | 4.2 (i.p.) |
| Desipramine | 2.3 (p.o.) |

Compounds I of the present invention are also useful as analgesic agents due to their ability to alleviate pain in mammals. The activity of the compounds is demonstrated in the 2-phenyl-1,4-benzoquinone-induced writhing (PQW) test in mice, a standard assay for analgesic [Proc. Soc. Exptl. Biol. Med., 95, 729 (1957)] and in modified Haffner's analgesia.

The latter assay is used to evaluate analgesic activity by measuring drug-induced changes in the sensitivity of mice to pressure stress by placing an artery clip (2½ inches long) on their tail. The procedure used is a modification of the test developed by Haffner, Dtsch. Med. Wschr. 55, 731 (1929), and it is described below.

METHOD

Male mice (Charles River, DC-1), from 18–30 grams are used for the test. An artery clip is applied to the root of the tail of a mouse (approximately ½ inch from the body) to induce pain. The animals quickly respond to this noxious stimuli by biting the clip or the location of the clip. This reaction time, the interval between stimulus onset and response, is recorded in 1/10 second increments by a stop watch.

For a time response, the screening dose (25 mg/kg) is administered subcutaneously (10 ml/kg) to the animal receiving food and water ad libitum before testing. Animals receiving the compound orally are fasted 18–24 hours before drug administration. Drug to be tested is prepared with distilled water and if insoluble, one drop of a surfactant is added.

Twenty-eight animals (seven/group) are administered the drug 15, 30, 45 and 60 minutes prior to testing.

The cut-off time (CO) is determined by taking the $X_{av}+3\sigma$ of the combined response latencies of the control mice in all time periods where $X_{av}$ is the average of X and $\sigma$ is the standard deviation.

$$CO = X_{av} + 3\sigma$$

Any reaction time, in subsequent drug tests, which is greater than the CO (for the same time period) therefore exceeds 99% of a normal Gaussian distribution and is called "positive response" indicative of analgesic activity. A time response indicates the period of greatest analgesic effect after dosing. The $ED_{50}$ is determined at the peak time of drug activity. A minimum of three dose groups are used. $ED_{50}$'s are calculated using computer analysis.

The results of some of the compounds of this invention are shown in Table 3 along with those of a prior art compound.

TABLE 3

ANALGESIC ACTIVITY ($ED_{50}$, mg/kg,s.c.)

| Compound | POW | Modified Haffner's Analgesia |
|---|---|---|
| N-methyl-N-(4-pyridinyl)-1H-indol-1-amine maleate | 3.2 | 16.3 |
| N-(4-pyridinyl)-1H-indol-1-amine maleate | 0.86 | 5.7 |
| N-propyl-N-(4-pyridinyl)-1H-indol-1-amine maleate | 5.1 | 31.0 |
| 3-ethyl-N-methyl-N-(4-pyridinyl)-1H-indol-1-amine hydrochloride | 0.9 | 1.0 |
| 3-ethenyl-N-methyl-N-(4-pyridinyl)-1H-indol-1-amine maleate | 1.0 | 1.0 |
| N-Methyl-5-nitro-N-(4-pyridinyl)-1H-indol-1-amine maleate | 1.0 | |

TABLE 3-continued

ANALGESIC ACTIVITY ($ED_{50}$, mg/kg,s.c.)

| Compound | POW | Modified Haffner's Analgesia |
|---|---|---|
| 3-Methyl-N-(4-pyridinyl)-1H-indol-1-amine oxalate | 0.4 | 0.7 |
| 3-Methyl-N-propyl-N-(4-pyridinyl)-1H-indol-1-amine maleate | 4.1 | 1.4 |
| N-(2-Propen-1-yl)-N-(4-pyridinyl)-1H-indol-1-amine maleate | 1.3 | 3.8 |
| (Prior Art Compoound) Pentazocine | 1.3 | 3.9 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, salicylic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
N-(4-pyridinyl)-1H-indol-1-amine;
N-methyl-N-(4-pyridinyl)-1H-indol-1-amine;
N-ethyl-N-(4-pyridinyl)-1H-indol-1-amine;
N-propyl-N-(4-pyridinyl)-1H-indol-1-amine;
5-methoxy-N-propyl-N-(4-pyridinyl)-1H-indol-1-amine;
N-methyl-N-(4-pyridinyl)-1H-indol-1-amine-3-carboxaldehyde;
N-ethyl-N-(4-pyridinyl)-1H-indol-1-amine-3-carboxaldehyde;
N-(4-nitro-3-pyridinyl)-1H-indol-1-amine-$N^1$-oxide;
N-(4-amino-3-pyridinyl)-1H-indol-1-amine-$N^1$-oxide;
3-ethenyl-N-methyl-N-(4-pyridinyl)-1H-indol-1-amine;
3-ethyl-N-methyl-N-(4-pyridinyl)-1H-indol-1-amine;
5-chloro-N-(4-pyridinyl)-1H-indol-1-amine;
5-chloro-N-propyl-N-(4-pyridinyl)-1H-indol-1-amine;
5-bromo-N-(4-pyridinyl)-1H-indol-1-amine;
5-bromo-N-methyl-N-(4-pyridinyl)-1H-indol-1-amine;
5-bromo-N-propyl-N-(4-pyridinyl)-1H-indol-1-amine;
5-Nitro-N-(4-pyridinyl)-1H-indol-1-amine;
N-Methyl-5-nitro-N-(4-pyridinyl)-1H-indol-1-amine;
3-Methyl-N-(4-pyridinyl)-1H-indol-1-amine;
3-Methyl-N-propyl-N-(4-pyridinyl)-1H-indol-1-amine;
N-(3-Fluoro-4-pyridinyl)-3-methyl-1H-indol-1-amine;
N-(3-Fluoro-4-pyridinyl)-N-propyl-3-methyl-1H-indol-1-amine;
N-(2-Propen-1-yl)-N-(4-pyridinyl)-1H-indol-1-amine;
N-(3-Fluoro-4-pyridinyl)-N-propyl-1H-indol-1-amine;
N-(3-Nitro-4-pyridinyl)-1H-indol-1-amine;
2-Methyl-N-(4-pyridinyl)-1H-indol-1-amine;
N-(3-Methyl-4-pyridinyl)-1H-indol-1-amine;
N-(3-Methyl-4-pyridinyl)-N-propyl-1H-indol-1-amine;
N-(3-Nitro-4-pyridinyl)-N-propyl-1H-indol-1-amine;
N-(3-Fluoro-4-pyridinyl)-1H-indol-1-amine;
N-(3-Chloro-4-pyridinyl)-1H-indol-1amine;
N-(3-Fluoro-4-pyridinyl)-2-methyl-1H-indol-1-amine;
N-(3-Chloro-4-pyridinyl)-3-methyl-1H-indol-1-amine;
3-Cyanomethyl-N-(4-pyridinyl)-1H-indol-1-amine;
5-Benzyloxy-N-(4-pyridinyl)-1H-indol-1-amine;
$N^3$-(1H-Indol-1-yl)-3,4-pyridinediamine;
$N^4$-(1H-indol-1-yl)-3,4-pyridinediamine;
$N^4$-(1H-Indol-1-yl)-$N^4$-propyl-3,4-pyridinediamine;
N-Propyl-N-(4-pyridinyl)-1H-indol-1-amine-3-carboxaldehyde;
α-Methyl-1-[[N-propyl-N-(4-pyridinyl)]amino]-1H-indol-3-methanol;
3-Acetyl-N-propyl-N-(4-pyridinyl)-1H-indol-1-amine;
3-(2-Amino-1-hydroxyethyl)-N-propyl-N-(4-pyridinyl)-1H-indol-1-amine;
N-Propyl-3-[(2-propynylimino)methyl]-N-(4-pyridinyl)-1H-indol-1-amine;
1-(Propyl-4-pyridinylamino)-N-2-propynyl-1H-indole-3-methanamine;
N-Propyl-N-(4-pyridinyl)-1H-indol-1-amine-3-carboxaldehyde oxime;
3-Aminomethyl-N-propyl-N-(4-pyridinyl)-1H-indol-1-amine;
N-Propyl-N-(4-pyridinyl)-3-ethenyl-1H-indol-1-amine;
3-Ethyl-N-propyl-N-(4-pyridinyl)-1H-indol-1-amine;
N-Butyl-N-(4-pyridinyl)-1H-indol-1-amine;
N-(2-Propynyl)-N-(4-pyridinyl)-1H-indol-1-amine;
N-(2-Methylpropyl)-N-(4-pyridinyl)-1H-indol-1-amine;
N-Pentyl-N-(4-pyridinyl)-1H-indol-1-amine;
N-(1-Methylpropyl)-N-(4-pyridinyl)-1H-indol-1-amine;
N-(3-Fluoropropyl)-N-(4-pyridinyl)-1H-indol-1-amine;
N-(1-Methylethyl)-N-(4-pyridinyl)-1H-indol-1-amine;
2-Methyl-N-propyl-N-(4-pyridinyl)-1H-indol-1-amine;
3-Cyanomethyl-N-propyl-N-(4-pyridinyl)-1H-indol-1-amine;
N-(3-Fluoro-4-pyridinyl)-N-(2-propenyl)-1H-3-methylindol-1-amine;
N-(3-Chloro-4-pyridinyl)-N-propyl-1H-indol-1-amine;
N-(3-Fluoro-4-pyridinyl)-N-(2-propynyl)-1H-indol-1-amine;
N-(3-Fluoro-4-pyridinyl)-3-methyl-N-(2-propynyl)-1H-indol-1-amine;
N-(3-Fluoro-4-pyridinyl)-2-methyl-N-propyl-1H-indol-1-amine;
N-(3-Chloro-4-pyridinyl)-3-methyl-N-propyl-1H-indol-1-amine;
N-(Dimethylaminopropyl)-N-(4-pyridinyl)-1H-indol-1-amine;
N-(3-Fluoro-4-pyridinyl)-N-(2-propenyl)-1H-indol-1-amine;
3-Cyano-N-propyl-N-(4-pyridinyl)-1H-indol-1-amine;
N-(3-Fluoro-4-pyridinyl)-N-[4-(pyrrolidin-1-yl)-2-butynyl]-1H-indol-1-amine;
3-(2-Aminoethyl)-N-(4-pyridinyl)-1H-indol-1-amine;
3-(2-Aminoethyl)-N-propyl-N-(4-pyridinyl)-1H-indol-1-amine;
3-[2-(Ethylamino)ethyl]-N-propyl-N-(4-pyridinyl)-1H-indol-1-amine;
N-[2-[1-(4-Pyridinylpropylamino)-1H-indol-3-yl]ethyl]acetamide;
3-(2-Aminopropyl)-N-propyl-N-(4-pyridinyl)-1H-indol-1-amine;
5-Benzyloxy-N-propyl-N-(4-pyridinyl)-1H-indol-1-amine;
5-Hydroxy-N-(4-pyridinyl)-1H-indol-1-amine;
5-Hydroxy-N-propyl-N-(4-pyridinyl)-1H-indol-1-amine;
3-Methyl-N-(3-methyl-4-pyridinyl)-1H-indol-1-amine;
3-Methyl-N-(3-methyl-4-pyridinyl)-N-propyl-1H-indol-1-amine;
2-Methyl-N-(3-methyl-4-pyridinyl)-1H-indol-1-amine;
2-Methyl-N-(3-methyl-4-pyridinyl)-N-propyl-1H-indol-1-amine;
N-[4-[4-(2-Methoxyphenyl)piperazin-1-yl]-2-butynyl]-N-(4-pyridinyl)-1H-indol-1-amine;

N-(4-Pyridinyl)-N-[4-(piperidin-1-yl)-2-butynyl]-1H-indol-1-amine;

N-[4-(Morpholin-4-yl)-2-butynyl]-N-(4-pyridinyl)-1H-indol-1-amine;

N-[1-(Propyl-4-pyridinylamino)-1H-indol-3-ylmethyl]acetamide;

N-[1-(Propyl-4-pyridinylamino)-1H-indol-3-ylmethyl]propionamide;

N-[1-(Propyl-4-pyridinylamino)-1H-indol-3-yl]methyl-N-2-propynylacetamide;

N-[1-(Propyl-4-pyridinylamino)-1H-indol-3-yl]methyl-N-[4-(pyrrolidin-1-yl)-2-butynyl]acetamide;

N-[4-(Piperidin-1-yl)-2-butynyl]-N-[1-(propyl-4-pyridinylamino)-1H-indol-3-ylmethyl]acetamide;

N-[4-[4-(2-Methoxyphenyl)-piperazin-1-yl]-2-butynyl]-N-[1-propyl-4-pyridinylamino)-1H-indol-3-ylmethyl]acetamide;

3-(2-Methoxyethenyl)-N-propyl-N-(4-pyridinyl)-1H-indol-1-amine;

3-(2-Phenylethenyl)-N-propyl-N-(4-pyridinyl)-1H-indol-1-amine;

N-Propyl-N-(4-pyridinyl)-3-[2-(2-thienyl)ethenyl]-1H-indol-1-amine;

N-Propyl-N-(4-pyridinyl)-3-[2-(4-pyridinyl)ethenyl]-1H-indol-1-amine;

N-Propyl-N-(4-pyridinyl)-3-[2-(4-pyridinyl)ethyl]-1H-indol-1-amine;

1-(Propyl-4-pyridinylamino)-1H-indol-3-ylmethyl acetate;

α-(4-Pyridinyl)1-(propyl-4-pyridinylamino)-1H-indol-3-methanol;

1-(Propyl-4-pyridinylamino)-3-(4-pyridinylmethyl)-1H-indol-1-amine; and 1-(Propyl-4-pyridinylamino)-1H-indol-3-methanol;

The following examples are presented in order to illustrate this invention.

EXAMPLE 1

N-(4-Pyridinyl)-1H-indol-1-amine maleate

A solution of 1H-indol-1-amine (30 g), 4-chlorpyridine hydrochloride (34 g) and pyridine (18 g) in 250 ml of isopropanol was stirred at 85° for 1.5 hours, and thereafter cooled, stirred with ice-water, basified with sodium carbonate and extracted with dichloromethane. The organic extract was washed with water and saturated sodium chloride solution, was dried over anhydrous magnesium sulfate, filtered and concentrated to a dark oil. This oil was purified by flash chromatography (silica, ethyl acetate) and thereafter by column chromatography (alumina, ether) to give 24 g of oil. A 3.6 g sample was purified by high performance liquid chromatography (HPLC hereafter) (silica, ethyl acetate) to give 3.5 g of oil. This oil was converted to the maleate salt and recrystallized twice from methanol/ether to give 3.8 g of needles, d 145°-146°.

ANALYSIS: Calculated for $C_{13}H_{11}N_3 \cdot C_4H_4O_4$: 62.76%C, 4.65%H, 12.92%N. Found: 62.62%C, 4.81%H, 12.73%N.

EXAMPLE 2

N-Methyl-N-(4-pyridinyl)-1H-indol-1-amine maleate

A solution of N-(4-pyridinyl)-1H-indol-1-amine (7.4 g) in 30 ml of dimethylformamide was added to an ice-cooled suspension of NaH (1.6 g of 60% NaH dispersion in mineral oil was washed with hexanes, the liquid portion was decanted and the residual solid was dispersed in 10 ml of dimethylformamide). After anion formation, a solution of dimethylsulfate (5 g) in 10 ml of dimethylformamide was added. After one hour of stirring at ambient temperature, the reaction mixture was stirred with ice-water and extracted with ether. The organic extract was washed with water and saturated sodium chloride solution, was dried over anhydrous magnesium sulfate, filtered and concentrated to 8 g of oil. This oil was purified by flash chromatography (silica, ethyl acetete), column chromatography (alumina, ether) and HPLC (silica, ethyl acetate) to give 2.9 g of oil. This oil was converted to the maleate salt and was recrystallized twice from methanol/ether to give 2.1 g of crystals, mp 103°-104°.

ANALYSIS: Calculated for $C_{14}H_{13}N_3 \cdot C_4H_4O_4$: 63.70%C, 5.05%H, 12.39%N. Found: 63.36%C, 4.93%H, 12.39%N.

EXAMPLE 3

N-Ethyl-N-(4-pyridinyl)-1H-indol-1-amine maleate

To an ice-cooled suspension of sodium hydride (1.7 g of 60% NaH dispersion in mineral oil was washed with hexanes, the liquid was decanted and the residual solid was dispersed in 5 ml of dimethylformamide) was slowly added a solution of N-(4-pyridinyl)-1H-indol-1-amine (7.6 g) in 25 ml of dimethylformamide. After anion formation, a solution of diethyl sulfate (6.4 g) in 10 ml of dimethylformamide was slowly added. After one hour, the mixture was stirred with ice-water and extracted with ethyl acetate. The organic extract was washed with water and saturated sodium chloride solution, was dried over anhydrous magnesium sulfate, filtered and concentrated to 11 g of oil. This oil was purified by flash chromatography (silica, ethyl acetate) to give 6.2 g of oil. This oil was purified by column chromatography (alumina, ether) to give 6 g of oil. A 3 g sample was converted to the maleate salt and recrystallized from ethanol/ether and thereafter from methanol/ether to give 2.7 g of crystals, mp 119°-120°.

ANALYSIS: Calculated for $C_{15}H_{15}N_3 \cdot C_4H_4O_4$: 64.58%C, 5.42%H, 11.89%N. Found: 64.27%C, 5.49%H, 12.11%N.

EXAMPLE 4

N-Propyl-N-(4-pyridinyl)-1H-indol-1-amine maleate

A solution of N-(4-pyridinyl)-1H-indol-1-amine (6 g) in 25 ml of dimethylformamide was slowly added to an ice-cooled suspension of NaH (1.3 g of 60% NaH dispersion in mineral oil was washed with hexanes, the liquid was decanted and the residual solid was dispersed in 5 ml of dimethylformamide). After anion formation, a solution of 1-bromopropane (4 g) in 5 ml of dimethylformamide was added. After one hour of stirring at ambient temperature, the reaction mixture was stirred with ice-water and extracted with dichloromethane. The organic extract was washed with water and saturated sodium chloride solution, was dried over anhydrous magnesium sulfate, filtered and concentrated to 8 g of oil. This oil was purified by HPLC (silica, ethyl acetate) and thereafter by column chromatography (alumina, ether) to give 6.4 g oil. This oil was converted to the maleate salt and recrystallized from methanol/ether to give 6.8 g of crystals, mp 115°-116°.

ANALYSIS: Calculated for $C_{16}H_{17}N_3 \cdot C_4H_4O_4$: 65.38%C, 5.76%H, 11.44%N. Found: 65.26%C, 5.71%H, 11.34%N.

EXAMPLE 5

5-Methoxy-N-propyl-N-(4-pyridinyl)-1H-indol-1-amine maleate

To an ice-cooled suspension of sodium hydride (0.5 g of 60% NaH dispersion in mineral oil was washed with hexanes, the liquid was decanted and the residual solid was dispersed in 5 ml of dimethylformamide) was slowly added a solution of 5-methoxy-N-(4-pyridinyl)-1H-indol-1-amine (2.3 g) in 20 ml of dimethylformamide. After anion formation, a solution of 1-bromopropane (1.4 g) in 5 ml of dimethylformamide was added. After one hour of stirring, the reaction mixture was stirred with ice-water and extracted with dichloromethane. The organic extract was washed with water and saturated sodium chloride solution, was dried over anhydrous magnesium sulfate, filtered and concentrated to 2.3 g of oil. This oil was purified by flash chromatography (silica, ethyl acetate) to give 2.1 g of oil. This oil was converted to the maleate salt in ethanol/ether to give 2.0 g of crystals, mp 138°–139°.

ANALYSIS: Calculated for $C_{17}H_{19}N_3O \cdot C_4H_4O_4$: 63.46%C, 5.83%H, 10.58%N. Found: 63.26%C, 5.77%H, 10.47%N.

EXAMPLE 6

N-Methyl-N-(4-pyridinyl)-1H-indol-1-amine-3-carboxaldehyde maleate

To ice-cooled dimethylformamide (4 g) was slowly added phosphorous oxychloride (7 g). After complex formation, a solution of N-methyl-N-(4-pyridinyl)-1H-indol-1-amine (5 g) in 50 ml of dichloroethane was added. After one hour of stirring at 85°, the reaction mixture was cooled, hydrolyzed with a solution of sodium acetate (5 g) in 25 ml of water, again cooled, basified with sodium carbonate and extracted with dichloromethane. The organic extract was washed with water and saturated sodium chloride solution, was dried over anhydrous magnesium sulfate, fitlered and concentrated to 6 g of oil. This oil was purified by flash chromatography (silica, ethyl acetate) to give 4.6 g of oil. This oil was converted to the maleate salt and recrystallized from ethanol/ether and thereafter from methanol/ether to give 2.6 g of crystals, d 162°–163°.

ANALYSIS: Calculated for $C_{15}H_{13}N_3O \cdot C_4H_4O_4$: 62.12%C, 4.66%H, 11.44%N. Found: 61.71%C, 4.62%H, 11.14%N.

EXAMPLE 7

N-Ethyl-N-(4-pyridinyl)-1H-indol-1-amine-3-carboxaldehyde maleate

To ice-cooled dimethylformamide (2.2 g) was slowly added phosphorous oxychloride (4.5 g). After complex formation, a solution of N-ethyl-N-(4-pyridinyl)-1H-indol-1(3.5 g) in 50 ml of dichloroethane was added. The mixture was stirred at 80° for one hour and thereafter hydrolyzed with a solution of sodium acetate (5 g) in 25 ml of water, cooled, basified with sodium carbonate and extracted with dichloromethane. The organic extract was washed with water and saturated sodium chloride solution, was dried over anhydrous magnesium sulfate, filtered and concentrated to 5 g of oil. This oil was purified by flash chromatography (silica, ethyl acetete) to give 3.5 g of oil. This oil was converted to the maleate salt and recrystallized from ethanol/ether and thereafter from methanol/ether to give 3 g of solid, d 170°–171°.

ANALYSIS: Calculated for $C_{16}H_{15}N_3O \cdot C_4H_4O_4$: 62.98%C, 5.02%H, 11.02%N. Found: 62.97%C, 5.08%H, 11.06%N.

EXAMPLE 8

N-(4-Nitro-3-pyridinyl)-1H-indol-1-amine $N^1$-oxide

A solution of 3-fluoro-4-nitro-pyridine-N-oxide (5 g) and 1H-indol-1-amine (4.2 g) in 25 ml of ethanol was stirred four hours at reflux. The solution was cooled and the product collected and dried to give 4 g of solid, d 195°. This material was recrystallized from ethanol/ether to give 2.2 g of solid, d 200°–201°.

ANALYSIS: Calculated for $C_{13}H_{10}N_4O_3$: 57.77%C, 3.73%H, 20.74%N. Found: 57.56%C, 3.74%H, 20.53%N.

EXAMPLE 9

N-(4-Amino-3-pyridinyl)-1H-indol-1-amine $N^1$-oxide

A mixture of N-(4-nitro-3-pyridinyl)-1H-indol-1-amine $N^1$-oxide (5 g) and 0.5 g of platinum oxide in 250 ml of ethanol was hydrogenated at 50 psi (pounds per square inch) for four hours. The mixture was filtered and the filtered liquid was concentrated to a dark residue which was purified by flash chromatography (silica, 10% methanol in dichloromethane) to give 2.5 g of solid, d 235°. This material was recrystallized from methanol/ether to give 2.1 g of crystals, d 235°.

ANALYSIS: Calculated for $C_{13}H_{12}N_4O$: 64.98%C, 5.03%H, 23.32%N. Found: 64.74%C, 5.12%H, 23.04%N.

EXAMPLE 10

3-Ethenyl-N-methyl-N-(4-pyridinyl)-1H-indol-1-amine maleate

To an ice-cooled suspension of methyltriphenylphosphonium bromide (13 g) in 100 ml of anhydrous ether was added potassium t-butoxide (4 g). After phosphorane formation, a solution of N-ethyl-N-(4-pyridinyl)-1H-indol-1-amine-3-carboxaldehyde (7.5 g) in 50 ml of ether and 50 ml of tetrahydrofuran was added. After one hour of stirring, the reaction mixture was stirred with water and extracted with ether. The organic extract was washed with water and saturated sodium chloride solution, was dried over anhydrous magnesium sulfate, filtered and concentrated to 20 g of oil. This oil was purified by flash chromatography (silica, ethyl acetate) to give 7 g of oil. A 3.5 g sample was converted to the maleate salt in ethanol and recrystallized from methanol/ether to give 3 g of crystals, mp 153°–154°.

ANALYSIS: Calculated for $C_{16}H_{15}N_3 \cdot C_4H_4O_4$: 65.74%C, 5.24%H, 11.50%N. Found: 65.94%C, 5.39%H, 11.45%N.

EXAMPLE 11

3-Ethyl-N-methyl-N-(4-pyridinyl)-1H-indol-1-amine hydrochloride

A solution of 3-ethenyl-N-methyl-N-(4-pyridinyl)-1H-indol-1-amine (5 g) in 250 ml of ethanol containing 0.5 g of platinum oxide was hydrogenated at 50 psi for one hour. The mixture was filtered and the filtered liquid was concentrated to 5 g of oil. This oil was purified by flash chromatography (silica, ethyl acetate) to give 3.5 g of oil. This oil was converted to the hydrochloride salt in ethanol/ether and recrystallized from methanol/ether to give 3.0 g of crystals, d 262°.

ANALYSIS: Calculated for $C_{16}H_{17}N_3.HCl$: 66.77%C, 6.30%H, 14.60%N. Found: 66.87%C, 6.33%H, 14.57%N.

EXAMPLE 12

5-Chloro-N-(4-pyridinyl)-1H-indol-1-amine maleate

A solution of 5-chloro-1H-indol-1-amine (9 g), 4-chloropyridine hydrochloride (12 g) and pyridine (6.4 g) in 100 ml of isopropanol was stirred at reflux for one hour, cooled and stirred with ice-water, and the mixture was basified with sodium carbonate, extracted with dichloromethane and filtered. The organic extract was washed with water and saturated sodium chloride, was dried over anhydrous magnesium sulfate, filtered and concentrated to a dark oil. This oil was purified by flash chromatography (silica, ethyl acetate) to give 6.2 g of oil. This oil was converted to the maleate salt in methanol-ether to give 7 g of crystals, mp 148°–150°. A 2.6 g sample was recrystallized from methanol-ether to give 2.4 g of crystals, d 150°–152°.

ANALYSIS: Calculated for $C_{13}H_{10}ClN_3.C_4H_4O_4$: 56.75%C, 3.92%H, 11.68%N. Found: 56.71%C, 4.00%H, 11.62%N.

EXAMPLE 13

5-Chloro-N-propyl-N-(4-pyridinyl)-1H-indol-1-amine maleate

A solution of 5-chloro-N-(4-pyridinyl)-1H-indol-1-amine (3.3 g) in 15 ml of dimethylformamide was slowly added to an ice-cooled suspension of sodium hydride (0.65 g of 60% oil dispersion was washed with hexanes) in 5 ml of dimethylformamide. After anion formation a solution of 1-bromopropane (2 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 5 g of oil. This oil was purified by flash chromatography (silica, ethyl acetate) to give 3.1 g of oil. This oil was converted to the maleate salt in ethanol-ether and thereafter recrystallized from methanol-ether to give 3.4 g of crystals, mp 130°.

ANALYSIS: Calculated for $C_{16}H_{16}ClN_3.C_4H_4O_4$: 59.77%C, 5.02%H, 10.46%N. Found: 59.97%C, 5.13%H, 10.35%N.

EXAMPLE 14

5-Bromo-N-(4-pyridinyl)-1H-indol-1-amine maleate

A solution of 5-bromo-1H-indol-1-amine (13 g), 4-chloropyridine hydrochloride (14 g) and pyridine (7.2 g) in 100 ml of isopropanol was stirred at reflux for one hour, cooled and stirred with ice-water, and thereafter the mixture was basified with sodium carbonate, extracted with dichloromethane and filtered. The organic extract was washed with water and saturated sodium chloride, was dried over anhydrous magnesium sulfate, filtered and concentrated to a dark oil. This oil was purified by flash chromatography (silica, ethyl acetate) to give 11 g of oil. This oil was converted to the maleate salt in ethanol-ether to give 13 g of solid, d 155°–157°. A three gram sample was recrystallized from methanol-ether to give 2.8 g of crystals, d 161°–162°.

ANALYSIS: Calculated for $C_{13}H_{10}BrN_3.C_4H_4O_4$: 50.51%C, 3.49%H, 10.40%N. Found: 50.46%C, 3.56%H, 10.40%N.

EXAMPLE 15

5-Bromo-N-methyl-N-(4-pyridinyl)-1H-indol-1-amine maleate

A solution of 5-bromo-N-(4-pyridinyl)-1H-indol-1-amine (2.7 g) in 20 ml of dimethylformamide was slowly added to an ice-cooled suspension of sodium hydride (0.45 g of 60% oil dispersion was washed with hexanes) in 5 ml of dimethylformamide. After anion formation a solution of dimethylsulfate (1.4 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 2 g of oil. This oil was purified by flash chromatography (silica, ethyl acetete) to give 1.4 g of oil. This oil was converted to the maleate salt in ethanol-ether to give 1.2 g of crystals, mp 110°–111°.

ANALYSIS: Calculated for $C_{14}H_{12}BrN_3.C_4H_4O_4$: 51.69%C, 3.86%H, 10.05%N. Found: 51.55%C, 3.89%H, 10.14%N.

EXAMPLE 16

5-Bromo-N-propyl-N-(4-pyridinyl)-1H-indol-1-amine maleate

A solution of 5-bromo-N-(4-pyridinyl)-1H-indol-1-amine (4.9 g) in 25 ml of dimethylformamide was slowly added to an ice-cooled suspension of sodium hydride (0.8 g of 60% oil dispersion was washed with hexanes) in 5 ml of dimethylformamide. After anion formation a solution of 1-bromopropane (2.5 g) in 5 ml of dimethylformamide was added. After one hour the reaction mixture was stirred with ice-water and extracted with dichloromethane. The organic extract was washed with water and saturated sodium chloride, was dried over anhydrous magnesium sulfate, filtered and concentrated to 5 g of oil. This oil was purified by flash chromatography (silica, ethyl acetate) to give 4.5 g of oil. This oil was converted to the maleate salt in ethanol-ether to give 5.4 g of solid, d 150°–152°. This solid was recrystallized from methanol-ether to give 4.8 g of crystals, d 157°–158°.

ANALYSIS: Calculated for $C_{16}H_{16}BrN_3.C_4H_4O_4$: 53.82%C, 4.52%H, 9.42%N. Found: 53.63%C, 4.62%H, 9.40%N.

EXAMPLE 17

5-Nitro-N-(4-pyridinyl)-1H-indol-1-amine hydrochloride

A solution of 5-nitro-1H-indol-1-amine (4.5 g) and 4-chloropyridine hydrochloride (4.5 g) in 175 ml of isopropanol was stirred at reflux for two hours, another equivalent of 4-chloropyridine hydrochloride was added and the mixture was refluxed for two additional hours. The reaction mixture was then cooled, stirred with water, basified with sodium carbonate and extracted with ethyl acetate. The organic extract was washed with water and saturated sodium chloride solution, was dried (MgSO₄), filtered and concentrated to 9 g of dark oil. This oil was purified by flash chromatography (silica, ethyl acetate) to give 3.8 g of light brown solid, m.p. 183°–184°. This material was converted to the hydrochloride salt and recrystallized twice from methanol/ether to give 3.5 g of orange needles, d 300°–302°.

ANALYSIS: Calculated for $C_{13}H_{10}N_4O_2 \cdot HCl$: 53.71%C, 3.81%H, 19.28%N. Found: 53.55%C, 3.77%H, 19.17%N.

EXAMPLE 18

N-Methyl-5-nitro-N-(4-pyridinyl)-1H-indol-1-amine maleate

A solution of 5-nitro-N-(4-pyridinyl)-1H-indol-1-amine (6 g) in 20 ml of dimethylformamide was slowly added to an ice-cooled NaH suspension prepared by washing 1.2 g of 60% NaH suspension in oil with hexanes and suspending the residue in 5 ml of dimethylformamide. After the anion formation a solution of dimethyl sulfate (3.7 g) in 10 ml of dimethylformamide was added. After one hour the reaction mixture was stirred with water and extracted with ethyl acetate. The organic extract was washed with water and saturated sodium chloride solution, was dried ($MgSO_4$), filtered and concentrated to 6 g of dark oil. This was purified by flash chromatography (silica, ethyl acetate) to give 2.7 g of orange solid, m.p. 149°–150°. This was converted to the maleate salt and recrystallized twice from methanol/ether to give 2.7 g of orange crystals, d 174°–175°.

ANALYSIS: Calculated for $C_{14}H_{12}N_4O_2 \cdot C_4H_4O_4$: 56.25%C, 4.20%H, 14.58%N. Found: 56.14%C, 4.27%H, 14.46%N.

EXAMPLE 19

3-Methyl-N-(4-pyridinyl)-1H-indol-1-amine oxalate

To 200 ml of isopropanol were added 4-chloropyridine hydrochloride (7.5 g) and 3-methyl-1H-indol-1-amine (7.6 g). The mixture was stirred at 90° C. for six hours, and thereafter poured into 400 ml of ice water, and stirred for five minutes. The pH was adjusted to 10 with $Na_2CO_3$ solution and then extracted with ethyl acetate. The organic layer was washed with water and dried (saturated NaCl, anhydrous $MgSO_4$).

After filtration, the solvent was evaporated to obtain 8.4 g of thick brown oil, which was eluted on a silica gel column with ethyl acetate via HPLC. The desired fractions were combined and concentrated to 7.4 g of brown oil.

A 2.3 g sample of this oil was dissolved in 50 ml of ethanol, and the pH adjusted to 1 with an ethanolic solution of oxalic acid, and the solution was diluted with ether. The resultant white precipitate was collected and dried to give 4.0 g, d @ 130°–135° C. This material was recrystallized from ethanol/ether (1:1) to give 3.8 g, d @ 137° C.

ANALYSIS: Calculated for $C_{14}H_{13}N_3 \cdot C_2H_2O_4$: 61.33%C 4.83%H 13.41%N Found: 61.41%C 4.96%H 13.28%N

EXAMPLE 20

3-Methyl-N-propyl-N-(4-pyridinyl)-1H-indol-1-amine maleate

To a cold NaH suspension prepared by washing 0.8 g of 60% NaH suspension in oil with hexanes and suspending the residue in 15 ml of dry DMF was added a solution of 3-methyl-N-(4-pyridinyl)-1H-indol-1-amine (4.0 g) in 25 ml of dry DMF in ten minutes. After ten minutes a solution of propyl bromide (2.7 g) in 15 ml DMF was added.

The mixture was stirred at ambient temperature for thirty minutes, poured into 200 ml of ice water, stirred for five minutes, and then extracted with ethyl acetate. The organic layer was washed with water and dried (saturated NaCl, anhydrous $MgSO_4$).

After filtration, the solvent was evaporated to give 5 g of brown oil, which was eluted on a silica gel column with ethyl acetate via HPLC. The desired fractions were combined and concentrated to 2.6 g of brown oil.

This oil was dissolved in ether, the pH was adjusted to 1 with ethereal maleic acid, and the resultant white precipitate collected and dried to give, 4.0 g d @ 148° C. This material was recrystallized from methanol/ether (1:10) to give 3.5 g of white crystals, m.p. 148°–149° C.

ANALYSIS: Calculated for $C_{17}H_{19}N_3 \cdot C_4H_4O_4$: 66.13%C 6.08%H 11.02%N Found: 66.15%C 6.02%H 11.00%N

EXAMPLE 21

N-(3-Fluoro-4-pyridinyl)-3-methyl-1H-indol-1-amine

To 200 ml of isopropanol were added 4-chloro-3-fluoropyridine hydrochloride (10 g) and 3-methyl-1H-indol-amine (5.9 g). The mixture was stirred at 90° C. for four hours, cooled, and poured into 500 ml of ice water. The pH was adjusted to 10 with $Na_2CO_3$ solution, and the mixture was extracted with ethyl acetate. The organic layer was washed with water and dried (saturated NaCl, anhydrous $MgSO_4$).

After filtration, the solvent was evaporated to give about 10 g of dark oil, which was eluted on a silica gel column first with dichloromethane, and then with ether/petroleum ether (1:1) via "flash chromatography". The desired fractions were combined and concentrated to a yellow solid, 6.2 g, m.p. 45° C. A sample of this material was recrystallized from isopropyl ether/hexanes (1:1) to give a yellow solid, m.p. 141°–142° C.

ANALYSIS: Calculated for $C_{14}H_{12}FN_3$: 69.69%C, 5.02%H, 17.42%N. Found: 69.52%C, 5.01%H, 17.57%N.

EXAMPLE 22

N-(3-Fluoro-4-pyridinyl)-N-propyl-3-methyl-1H-indol-1-amine hydrochloride

To a NaH suspension prepared by washing 0.5 g of 60% NaH suspension in oil with hexanes and suspending the residue in 10 ml of DMF, was added a solution of N-(3-fluoro-4-pyridinyl)-3-methyl-1H-indol-1-amine (3.0 g) in 20 ml of DMF at ice-bath temperature in ten minutes. The mixture was stirred for an additional five minutes, and thereafter a solution of propyl bromide (1.2 ml) in 10 ml of DMF was added in five minutes.

The mixture was stirred at ambient temperature for thirty minutes, poured into 10 ml of ice-water, and then extracted with ethyl acetate. The organic layer was collected, washed with water, and dried (saturated NaCl, anhydrous $MgSO_4$).

After filtration, the solvent was evaporated to give 4 g of brown oil, which was eluted on a silica gel column with 20% ethyl acetate/DCM via HPLC. The desired fractions were combined and concentrated to a thick yellow oil, 3.4 g.

The oil was dissolved in ether, the pH adjusted to 1 with ethereal-HCl, and the resultant white precipitate collected and dried to give 3.4 g. This material was recrystallized from ethanol/ether (1:20) to give 2.7 g of white crystals, d @ 193° C.

ANALYSIS: Calculated for $C_{17}H_{18}FN_3 \cdot HCl$: 63.84%C 5.99%H 13.14%N Found: 64.11%C 6.01%H 13.20%N

EXAMPLE 23

N-(2-Propen-1-yl)-N-(4-pyridinyl)-1H-indol-1-amine maleate

A solution of N-(4-pyridinyl)-1H-indol-1-amine (8 g) in 40 ml of dimethylformamide was added to an ice-cooled NaH suspension prepared by washing 2 g of 60% NaH suspension in oil with hexanes and suspending the residue in 10 ml of dimethylformamide. After the anion formation a solution of allyl bromide (6 g) in 10 ml of dimethylformamide was added. After one hour the reaction mixture was stirred with ice-water and extracted with ethyl acetate. The organic extract was washed with water and saturated sodium chloride, dried (MgSO$_4$), filtered and concentrated to an oil. This oil was purified first by flash chromatography (silica, ethyl acetate) and then by column chromatography (alumina, ether) to give 5 g of oil. This oil was converted to the maleate salt in methanol/ether to give 6 g of pale yellow solid, m.p. 105°–107°. This was combined with 1.8 g product from a previous reaction and recrystallized from methanol/ether to give 5 g of pale yellow crystals, m.p. 111°–112°.

ANALYSIS; Calculated for $C_{16}H_{15}N_3 \cdot C_4H_4O_4$: 65.74%C, 5.24%H, 11.50%N. Found: 65.80%C, 5.24%H, 11.51%N.

EXAMPLE 24

N-(3-Fluoro-4-pyridinyl)-N-propyl-1H-indol-1-amine hydrochloride

To a NaH suspension prepared by washing 0.6 g of 60% NaH suspension in oil with hexanes and suspending the residue in 10 ml of cold DMF, was added a solution of N-(3-fluoro-4-pyridinyl)-1H-indol-1-amine in 25 ml of DMF.

The mixture was stirred at 5° C. for ten minutes, and thereafter a solution of bromopropane (1.4 ml) in 10 ml of DMF was added.

The mixture was stirred at ambient temperature for thirty minutes, poured into 200 ml of ice water, stirred for five minutes, and extracted with ethyl acetate. The organic layer was washed with water and dried (saturated NaCl, anhydrous MgSO$_4$).

After filtration, the solvent was evaporated to give 3.2 g of brown oil, which was eluted on a silica gel column with 10% ethyl acetate/DCM via HPLC. The desired fractions were combined and concentrated to 2.4 g of brown oil, which was dissolved in 40 ml of absolute ethanol. The pH was adjusted to 1 with ethereal-HCl, and the solution was diluted with 400 ml of ether. The resultant off-white precipitate was collected and dried to give 2.1 g, m.p. 198°–200° C. dec.

ANALYSIS: Calculated for $C_{16}H_{16}FN_3 \cdot HCl$: 62.85%C, 5.60%H, 13.74%N. Found: 62.80%C, 5.60%H, 13.66%N.

EXAMPLE 25

3-Cyanomethyl-1H-indol-1-amine

To a cold solution of 3-cyanomethyl-1H-indole (25 g) in 200 ml dimethylformamide (DMF), was added milled KOH (48 g) portionwise maintaining the temperature at 0° to 5° C.

After cooling to 0° C., hydroxylamine-1-sulfonic acid (23 g) was added portionwise, maintaining the temperature at 10°–15° C. Thereafter, the mixture was stirred at 5° C. for one hour.

After filtering, the filtrate was poured into 500 ml iced-water, stirred for five minutes, and extracted with ethyl acetate (3×). The organic layer was washed with water (2×) and dried (saturated NaCl, anhydrous MgSO$_4$).

After filtering, the solvent was evaporated to afford an oil, 30 g, which was eluted on a silica gel column with 25% hexane/DCM via HPLC. The desired fractions were combined and concentrated to a thick oil, which solidified to afford 13 g of solid, m.p. 88°–90° C.

EXAMPLE 26

N-(3-Nitro-4-pyridinyl)-1H-indol-1-amine

The title compound was prepared from 1H-indol-1-amine and 4-chloro-3-nitropyridine in ethanol at 70° C. for 3 hours in substantially the same manner as in Example 1. Recrystallized from ethanol, m.p. 170°–172° C.

ANALYSIS: Calculated for $C_{13}H_{10}N_4O_2$: 61.41%C, 3.96%H, 22.04%N. Found: 61.25%C, 3.80%H, 21.91%N.

EXAMPLE 27

2-Methyl-N-(4-pyridinyl)-1H-indol-1-amine

The title compound was prepared from 2-methyl-1H-indol-1-amine and 4-chloropyridine hydrochloride at 120° C. for 30 minutes in substantially the same manner as in Example 1, m.p. 75°–78° C.

ANALYSIS: Calculated for $C_{14}H_{13}N_3$: 75.31%C, 5.87%H, 18.82%N. Found: 75.02%C, 5.88%H, 18.66%N.

EXAMPLE 28

N-(3-Methyl-4-pyridinyl)-1H-indol-1-amine

The title compound was prepared from 1H-indol-1-amine and 4-chloro-3-methylpyridine hydrochloride in isopropanol at 90° C. for 6 hours in substantially the same manner as in Example 1, m.p. 78°–80° C.

ANALYSIS: Calculated for $C_{14}H_{13}N_3$: 75.31%C, 5.87%H, 18.82%N. Found: 74.98%C, 5.83%H, 18.86%N.

EXAMPLE 29

N-(3-Methyl-4-pyridinyl)-N-propyl-1H-indol-1-amine oxalate

The title compound was prepared from N-propyl-1H-indol-1-amine and 4-chloro-3-methylpyridine hydrochloride in 1-methyl-2-pyrrolidinone at 120° C. for 20 hours in substantially the same manner as in Example 1, d @155° C.

ANALYSIS: Calculated for $C_{17}H_{19}N_3 \cdot C_2H_2O_4$: 64.21%C, 5.96%H, 11.82%N. Found: 64.15%C, 5.85%H, 11.69%N.

EXAMPLE 30

N-(3-Nitro-4-pyridinyl)-N-propyl-1H-indol-1-amine

The title compound was prepared from N-propyl-1H-indol-1-amine and 4-chloro-3-nitropyridine in 1-methyl-2-pyrrolidinone at 100° C. for 4 hours in substantially the same manner as in Example 1, m.p. 84°–86° C.

ANALYSIS: Calculated for $C_{16}H_{16}N_4O_2$: 64.85%C, 5.44%H, 18.91%N. Found: 64.85%C, 5.51%H, 18.79%N.

EXAMPLE 31

N-(3-Fluoro-4-pyridinyl)-1H-indol-1-amine hydrochloride

The title compound was prepared from 1H-indol-1-amine and 4-chloro-3-fluoropyridine hydrochloride in isopropanol at 90° C. for 4 hours in substantially the same manner as in Example 1, m.p. >250° C.

ANALYSIS: Calculated for $C_{13}H_{10}FN_3 \cdot HCl$: 59.21%C, 4.21%H, 15.93%N. Found: 59.35%C, 4.36%H, 15.81%N.

EXAMPLE 32

N-(3-Chloro-4-pyridinyl)-1H-indol-1-amine hydrochloride

The title compound was prepared from 1H-indol-1-amine and 3,4-dichloropyridine hydrochloride in isopropanol at 100° C. for 4 hours in substantially the same manner as in Example 1, m.p. >230° C.

ANALYSIS: Calculated for $C_{13}H_{10}ClN_3 \cdot HCl$: 55.73%C, 3.96%H, 15.00%N. Found: 55.97%C, 4.23%H, 14.64%N.

EXAMPLE 33

N-(3-Fluoro-4-pyridinyl)-2-methyl-1H-indol-1-amine

The title compound was prepared from 2-methyl-1H-indol-1-amine and 4-chloro-3-fluoropyridine hydrochloride in 1-methyl-2-pyrrolidone for 1 hour in substantially the same manner as in Example 1, m.p. 157°–158° C.

ANALYSIS: Calculated for $C_{14}H_{12}FN_3$: 69.69%C, 5.02%H, 17.42%N. Found: 69.53%C, 4.95%H, 17.28%N.

EXAMPLE 34

N-(3-Chloro-4-pyridinyl)-3-methyl-1H-indol-1-amine hydrochloride

The title compound was prepared from 3-methyl-1H-indol-1-amine and 3,4-dichloropyridine in isopropanol at 80° C. for 5 hours in substantially the same manner as in Example 1. Recrystallized from ethanol, m.p. 278°–280° C. (decomp.).

ANALYSIS: Calculated for $C_{14}H_{12}ClN_3 \cdot HCl$: 57.16%C, 4.45%H, 14.29%N. Found: 57.20%C, 4.44%H, 14.28%N.

EXAMPLE 35

3-Cyanomethyl-N-(4-pyridinyl)-1H-indol-1-amine

The title compound was prepared from 3-cyanomethyl-1H-indol-1-amine and 4-chloropyridine hydrochloride in isopropanol at 90° C. for 6 hours in substantially the same manner as in Example 1, m.p. 80°–83° C.

ANALYSIS: Calculated for $C_{15}H_{12}N_4$: 72.56%C, 4.87%H, 22.59%N. Found: 72.41%C, 4.86%H, 22.16%N.

EXAMPLE 36

5-Benzyloxy-N-(4-pyridinyl)-1H-indol-1-amine

The title compound was prepared from 5-benzyloxy-1H-indol-1-amine (which had been prepared from 5-benzyloxy-1H-indole and hydroxylamine-O-sulfonic acid in substantially the same manner as in Example 25) and 4-chloropyridine hydrochloride in N-methyl-2-pyrrolidinone at 70° C. for 1.5 hours in substantially the same manner as in Example 1, m.p. 143°–145° C.

EXAMPLE 37

N-Propyl-N-(4-pyridinyl)-1H-indol-1-amine-3-carboxaldehyde maleate

The title compound was prepared from N-propyl-N-(4-pyridinyl)-1H-indol-1-amine, phosphorous oxychloride and dimethylformamide in substantially the same manner as in Example 6, m.p. 169°–171° C.

ANALYSIS: Calculated for $C_{21}H_{21}N_3O_5$: 63.79%C, 5.35%H, 10.63%N. Found: 63.67%C, 5.38%H, 10.58%N.

EXAMPLE 38

α-Methyl-1-[[N-propyl-N-(4-pyridinyl)]amino]-1H-indol-3-methanol

A solution of methylmagnesium bromide (3.2M in ether, 15 ml) was added to a solution of N-propyl-N-(4-pyridinyl)-1H-indol-1-amine-3-carboxaldehyde (4 g) in 300 ml anhydrous ether. After stirring one hour at ambient temperature the mixture was hydrolyzed by stirring with a solution of ammonium chloride (20 g) in 400 ml water and thereafter basified with sodium carbonate and extracted with ether. The organic extract was washed with water and saturated sodium chloride solution, dried (anhy. $MgSO_4$), filtered and concentrated to 4.5 g oil. This oil was purified by flash chromatography to give 3.8 g solid, m.p. 114°–116°. This solid was recrystallized from diethyl ether to give 2.5 g crystals, m.p. 115°–117° C.

ANALYSIS: Calculated for $C_{18}H_{21}N_3O$: 73.19%C, 7.17%H, 14.23%N. Found: 73.43%C, 7.22%H, 14.28%N.

EXAMPLE 39

3-Acetyl-N-propyl-N-(4-pyridinyl)-1H-indol-1-amine

Pyridinium dichromate (13 g) was added to a solution of α-methyl-1-[[N-propyl-N-(4-pyridinyl)]amino]-1H-indol-3-methanol (8 g). After stirring one hour at ambient temperature the mixture was stirred with water, basified with sodium carbonate, extracted with ether and filtered. The organic extract was washed with water and saturated sodium chloride solution, dried (anhy. $MgSO_4$), filtered and concentrated to 8.5 g oil. This oil was purified by flash chromatography to give 6.5 g oil. This oil was triturated with methanol to give 5.5 g solid, m.p. 81°–86° C. This solid was recrystallized twice from methanol to yield 2.5 g crystals, m.p. 103°–105° C.

ANALYSIS: Calculated for $C_{18}H_{19}N_3O$: 73.70%C, 6.53%H, 14.32%N. Found: 73.66%C, 6.51%H, 14.42%N.

EXAMPLE 40

3-(2-Amino-1-hydroxyethyl)-N-propyl-N-(4-pyridinyl)-1H-indol-1-amine

To a solution of N-propyl-N-(4-pyridinyl)-1H-indol-1-amine-3-carboxaldehyde (10 g) in 75 ml dichloroethane was added ZnI$_2$ (0.25 g) followed by trimethylsilyl cyanide (5 ml).

After stirring at 90° C. for 6 hours, the mixture was concentrated to an oil, which was dissolved in 100 ml THF. The solution was added to a cold solution of LiAlH$_4$ (0.04 mole) in 30 ml THF. After stirring at 60° C. for 1 hour, the mixture was cooled, poured into 200 ml iced NH$_4$Cl solution, and extracted with ethyl acetate. The organic layer was washed with water (2×) and dried (saturated NaCl, anhydrous MgSO$_4$).

After filtering, the filtrate was concentrated to an oil, 8 g, which was eluted on a silica gel column with 50% methanol/DCM via HPLC. The desired fractions were combined and concentrated to an oil, 3 g. This oil was eluted on an alumina column with ethyl acetate to give an oil, 2.3 g.

ANALYSIS: Calculated for C$_{18}$H$_{22}$N$_4$O: 69.65%C, 7.15%H, 18.05%N. Found: 69.25%C, 7.48%H, 17.79%N.

EXAMPLE 41

N-Propyl-3-[(2-propynylimino)methyl]-N-(4-pyridinyl)-1H-indol-1-amine

A solution of N-propyl-N-(4-pyridinyl)-1H-indol-1-amine-3-carboxaldehyde (14.6 g) and propargylamine (15 g) in 200 ml benzene was heated at reflux for 5 hours with removal of water. The mixture was concentrated to afford 17 g of oil.

This oil was eluted with ether through alumina via column chromatography to yield 16 g oil. This oil was triturated with hexane-ether to yield a solid, m.p. 86°–89° C.

EXAMPLE 42

1-(Propyl-4-pyridinylamino)-N-(2-propynyl)-1H-indol-3-methanamine dimaleate

A solution of N-propyl-3-[(2-propynylimino)methyl]-N-(4-pyridinyl)-1H-indol-1-amine (13 g) and sodium borohydride (4 g) in 125 ml isopropanol and 25 ml methanol was stirred three hours at ambient temperature. After cooling, the solution was stirred with water and extracted with ethyl acetate. The organic extract was washed with water and saturated sodium chloride solution, dried (anhydrous magnesium sulfate), filtered and concentrated to 13 g oil. This was combined with 1.5 g product obtained from a trial reduction and eluted with ethyl acetate through silica via flash column chromatography to yield 13.5 g oil. This oil was eluted with ethyl acetate through silica via HPLC to yield 12 g oil. A 4.4 g portion was converted to the dimaleate salt in methanol-ether to yield 4.1 g solid, m.p. 146°–147° C. This was recrystallized from methanol-ether to yield 3.7 g crystals, m.p. 146°–148° C.

ANALYSIS: Calculated for C$_{28}$H$_{30}$N$_4$O$_8$: 61.08%C, 5.49%H, 10.18%N. Found: 60.91%C, 5.32%H, 10.12%N.

EXAMPLE 43

N-Propyl-N-(4-pyridinyl)-1H-indol-1-amine-3-carboxaldehyde oxime maleate

To a solution of N-propyl-N-(4-pyridinyl)-1H-indol-1-amine-3-carboxaldehyde (10 g) in 100 ml pyridine was added hydroxylamine hydrochloride (5 g). After stirring one hour at ambient temperature the reaction mixture was concentrated and the residue was stirred with water, basified with sodium carbonate and extracted with ethyl acetate/ether. The organic extract was washed with water and saturated sodium chloride solution, dried (anhy. MgSO$_4$), filtered and concentrated to 12 g oil. This oil was purified by flash chromatography to give 10.3 g oil. A 3.5 g portion was converted to the maleate salt in ethanol/ether to give 4 g solid, d 147°–149° C. This solid was recrystallized from ethanol/ether to give 3.5 g solid, d 155°–156° C.

ANALYSIS: Calculated for C$_{21}$H$_{22}$N$_4$O$_5$: 61.46%C, 5.40%H, 13.65%N. Found: 61.39%C, 5.24%H, 13.34%N.

EXAMPLE 44

3-Aminomethyl-N-propyl-N-(4-pyridinyl)-1H-indol-1-amine dihydrochloride

A solution of N-propyl-N-(4-pyridinyl)-1H-indol-1-amine-3-carboxaldehyde oxime (5.5 g) in 100 ml 95% ethanol was quickly treated with Raney alloy (7.3 g, 50:50 Al/Ni alloy) and then with a solution of sodium hydroxide (7.8 g) in 100 ml water. The exothermic reaction was controlled with a reflux condenser. The mixture was cooled to ambient temperature and stirred for 2 hours. The Raney nickel catalyst (pyrophoric) was removed by filtration and the filtrate was washed with 50% aqueous ethanol. The filtrate was concentrated to remove the ethanol and the aqueous residue was extracted with dichloromethane. The organic extract was washed with water and saturated sodium chloride solution. The dried (anhy. MgSO$_4$) organic layer was concentrated to 4.7 g oil. This was combined with 0.9 g product obtained from a trail reduction and eluted with 20% methanol in dichloromethane through silica via flash column chromatography to yield 4.3 g oil. This oil was converted to the dihydrochloride salt in methanol and thereafter the methanol was evaporated. The residue was recrystallized from 20% methanol in acetonitrile to yield 4 g solid, m.p. 254°–256° C. This solid was recrystallized from 20% methanol in acetonitrile to yield 2.9 g solid, m.p. 254°–256° C.

ANALYSIS: Calculated for C$_{17}$H$_{22}$Cl$_2$N$_4$: 57.79%C, 6.28%H, 15.86%N. Found: 57.69%C, 6.05%H, 15.85%N.

EXAMPLE 45

N-Propyl-N-(4-pyridinyl)-3-ethenyl-1-H-indol-1-amine maleate

The title compound was prepared from N-propyl-N-(4-pyridinyl)-1H-indol-1-amine-3-carboxaldehyde, methyltriphenylphosphonium bromide and potassium-t-butoxide in substantially the same manner as in Example 10. Recrystallized from methanol/ether, m.p. 157°–158° C. (decomp.).

ANALYSIS: Calculated for C$_{18}$H$_{19}$N$_3$·C$_4$H$_4$O$_4$: 67.16%C, 5.89%H, 10.68%N. Found: 66.87%C, 5.76%H, 10.56%N.

EXAMPLE 46

3-Ethyl-N-propyl-N-(4-pyridinyl)-1H-indol-1-amine maleate

The title compound was prepared by hydrogenating 3-ethenyl-N-propyl-N-(4-pyridinyl)-1H-indol-1-amine in substantially the same manner as in Example 11, m.p. 133°–134° C.

ANALYSIS: Calculated for C$_{18}$H$_{21}$N$_3$·C$_4$H$_4$O$_4$: 66.82%C, 6.37%H, 10.63%N. Found: 66.73%C, 6.40%H, 10.62%N.

EXAMPLE 47

N-Butyl-N-(4-pyridinyl)-1H-indol-1-amine maleate

The title compound was prepared from N-(4-pyridinyl)-1H-indol-1-amine and 1-bromobutane with the aid of NaH in substantially the same manner as in Example 4. Recrystallized from ethanol/ether (1:10), m.p. 108°–110°.

ANALYSIS: Calculated for $C_{17}H_{19}N_3 \cdot C_4H_4O_4$: 66.13%C, 6.08%H, 11.02%N. Found: 66.10%C, 6.05%H, 11.04%N.

EXAMPLE 48

N-(2-Propynyl)-N-(4-pyridinyl)-1H-indol-1-amine maleate

The title compound was prepared from N-(4-pyridinyl)-1H-indol-1-amine and propargyl bromide with the aid of NaH in substantially the same manner as in Example 4. Recrystallized from ethanol/ether, m.p. 107°–109° C.

ANALYSIS: Calculated for $C_{16}H_{13}N_3 \cdot C_4H_4O_4$: 66.11%C, 4.72%H, 11.56%N. Found: 66.04%C, 4.69%H, 11.45%N.

EXAMPLE 49

N-(2-Methylpropyl)-N-(4-pyridinyl)-1H-indol-1-amine maleate

The title compound was prepared from N-(4-pyridinyl)-1H-indol-1-amine and 1-bromo-3-methylpropane with the aid of NaH in substantially the same manner as in Example 4, m.p. 101°–103° C.

ANALYSIS: Calculated for $C_{21}H_{23}N_3O_4$: 66.13%C, 6.08%H, 11.02%N. Found: 66.03%C, 6.09%H, 11.01%N.

EXAMPLE 50

N-Pentyl-N-(4-pyridinyl)-1H-indol-1-amine maleate

The title compound was prepared from N-(4-pyridinyl)-1H-indol-1-amine and 1-bromopentane with the aid of NaH in substantially the same manner as in Example 4. Recrystallized from ethanol/ether (1:9), m.p. 91°–93° C.

ANALYSIS: Calculated for $C_{22}H_{25}N_3O_4$: 66.82%C, 6.37%H, 10.63%N. Found: 66.70%C, 6.29%H, 10.55%N.

EXAMPLE 51

N-(1-Methylpropyl)-N-(4-pyridinyl)-1H-indol-1-amine maleate

The title compound was prepared from N-(4-pyridinyl)-1H-indol-1-amine and 2-bromobutane with the aid of NaH in substantially the same manner as in Example 4. Recrystallized from ethanol/ether, m.p. 117°–118° C.

ANALYSIS: Calculated for $C_{21}H_{23}N_3O_4$: 66.13%C, 6.08%H, 11.02%N. Found: 65.78%C, 5.97%H, 10.98%N.

EXAMPLE 52

N-(3-Fluoropropyl)-N-(4-pyridinyl)-1H-indol-1-amine maleate

The title compound was prepared from N-(4-pyridinyl)-1H-indol-1-amine and 1-bromo-3-fluoropropane with the aid of NaH in substantially the same manner as in Example 4, m.p. 117°–118° C.

ANALYSIS: Calculated for $C_{20}H_{20}FN_3O_4$: 62.33%C, 5.23%H, 10.90%N. Found: 62.37%C, 5.20%H, 10.83%N.

EXAMPLE 53

N-(1-Methylethyl)-N-(4-pyridinyl)-1H-indol-1-amine maleate

The title compound was prepared from N-(4-pyridinyl)-1H-indol-1-amine and 2-bromopropane with the aid of NaH in substantially the same manner as in Example 4. Recrystallized from methanol/ether, m.p. 121°–123° C.

ANALYSIS: Calculated for $C_{20}H_{21}N_3O_4$: 65.38%C, 5.76%H, 11.44%N. Found: 65.28%C, 5.81%C, 11.36%N.

EXAMPLE 54

2-Methyl-N-propyl-N-(4-pyridinyl)-1H-indol-1-amine maleate

The title compound was prepared from 2-methyl-N-(4-pyridinyl)-1H-indol-1-amine and 1-bromopropane with the aid of NaH in substantially the same manner as in Example 4, m.p. 155°–156° C. (decomp.).

ANALYSIS: Calculated for $C_{21}H_{23}N_3O_4$: 66.13%C, 6.08%H, 11.02%N. Found: 65.78%C, 6.08%H, 10.82%N.

EXAMPLE 55

3-Cyanomethyl-N-propyl-N-(4-pyridinyl)-1H-indol-1-amine hydrochloride

The title compound was prepared from 3-cyanomethyl-N-(4-pyridinyl)-1H-indol-1-amine and 1-bromopropane with the aid of NaH in substantially the same manner as in Example 4.

ANALYSIS: Calculated for $C_{18}H_{19}ClN_4$: 66.15%C, 5.86%H, 17.14%N. Found: 65.94%C, 5.89%H, 16.85%N.

EXAMPLE 56

N-(3-Fluoro-4-pyridinyl)-N-(2-propenyl)-3-methyl-1H-indol-1-amine hydrochloride

The title compound was prepared from N-(3-fluoro-4-pyridinyl)-3-methyl-1H-indol-1-amine and allyl bromide with the aid of NaH in substantially the same manner as in Example 4, m.p. 185°–187° C.

ANALYSIS: Calculated for $C_{17}H_{16}FN_3 \cdot HCl$: 64.25%C, 5.39%H, 13.22%N. Found: 64.15%C, 5.39%H, 13.08%N.

EXAMPLE 57

N-(3-Chloro-4-pyridinyl)-N-propyl-1H-indol-1-amine hydrochloride

The title compound was prepared from N-(3-chloro-4-pyridinyl)-N-propyl-1H-indol-1-amine and propyl bromide with the aid of NaH in substantially the same manner as in Example 4, m.p. 202° C. (decomp.).

ANALYSIS: Calculated for $C_{16}H_{16}ClN_3 \cdot HCl$: 59.63%C, 5.32%H, 13.04%N. Found: 60.01%C, 5.31%H, 12.94%N.

EXAMPLE 58

N-(3-Fluoro-4-pyridinyl)-N-(2-propynyl)-1H-indol-1-amine hydrochloride

The title compound was prepared from N-(3-fluoro-4-pyridinyl)-1H-indol-1-amine and propargyl bromide with the aid of NaH in substantially the same manner as in Example 4. Recrystallized from methanol/ether (1:5), m.p. 211°-212° C.

ANALYSIS: Calculated for $C_{16}H_{12}FN_3 \cdot HCl$: 63.68%C, 4.34%H, 13.93%N. Found: 63.46%C, 4.20%H, 13.72%N.

EXAMPLE 59

N-(3-Fluoro-4-pyridinyl)-3-methyl-N-(2-propynyl)-1H-indol-1-amine hydrochloride

The title compound was prepared from N-(3-fluoro-4-pyridinyl)-3-methyl-1H-indol-1-amine and propargyl bromide with the aid of NaH in substantially the same manner as in Example 4. Recrystallized from methanol/ether (1:5), m.p. 206°-207° C.

ANALYSIS: Calculated for $C_{17}H_{14}FN_3 \cdot HCl$: 64.66%C, 4.79%H, 13.30%N. Found: 64.49%C, 4.70%H, 13.18%N.

EXAMPLE 60

N-(3-Fluoro-4-pyridinyl)-2-methyl-N-propyl-1H-indol-1-amine

The title compound was prepared from N-(3-fluoro-4-pyridinyl)-2-methyl-1H-indol-1-amine and 1-bromopropane with the aid of NaH in substantially the same manner as in Example 4, m.p. 5° C.

ANALYSIS: Calculated for $C_{17}H_{18}FN_3$: 72.06%C, 6.40%H, 14.83%N. Found: 71.76%C, 6.51%H, 14.48%N.

EXAMPLE 61

N-(3-Chloro-4-pyridinyl)-3-methyl-N-propyl-1H-indol-1-amine

The title compound was prepared from N-(3-chloro-4-pyridinyl)-3-methyl-1H-indol-1-amine and 1-bromopropane with the aid of NaH in substantially the same manner as in Example 4, m.p. 68°-70°.

ANALYSIS: Calculated for $C_{17}H_{18}ClN_3$: 68.10%C, 6.05%H, 14.02%N. Found: 67.99%C, 6.01%H, 14.01%N.

EXAMPLE 62

N-(Dimethylaminopropyl)-N-(4-pyridinyl)-1H-indol-1-amine

The title compound was prepared from N-(4-pyridinyl)-1H-indol-1-amine and dimethylaminopropyl chloride with the aid of NaH in substantially the same manner as in Example 4. The product was obtained as an oil.

EXAMPLE 63

N-(3-Fluoro-4-pyridinyl)-N-(2-propenyl)-1H-indol-1-amine hydrochloride

To a cold solution of N-(3-fluoro-4-pyridinyl)-1H-indol-1-amine (2.9 g) in 70 ml of dry THF was added potassium t-butoxide (1.7 g), and the mixture was stirred at 0° C. for ten minutes. To this was added a solution of allyl bromide (1.3 ml) in 10 ml THF.

After stirring at 0° C. for 2 hours, the mixture was poured into 100 ml water, stirred for 5 minutes and extracted with ethyl acetate (3×). The organic layer was washed with water and dried (saturated NaCl, anhydrous MgSO₄).

After filtering, the filtrate was concentrated to an oil, 3.0 g; which was eluted on a silica gel column with 50% ethyl acetate/DCM via HPLC. The desired fractions were combined and concentrated to an oil, 2.0 g, which was dissolved in ethanol. The pH was adjusted to 1 with ethereal HCl, and the solution was diluted with ether. The resultant precipitate was collected and dried to give 2.0 g, m.p. 204°-205° C.

ANALYSIS: Calculated for $C_{16}H_{14}FN_3 \cdot HCl$: 63.26%C, 4.98%H, 13.83%N. Found: 63.25%C, 4.98%H, 13.70%N.

EXAMPLE 64

3-Cyano-N-propyl-N-(4-pyridinyl)-1H-indol-1-amine maleate

To a solution of N-propyl-N-(4-pyridinyl)-1H-indol-1-amine-3-carboxaldehyde oxime (8 g) in 125 ml ether and pyridine (5 g) was added benzenesulfonyl chloride (6 g). The mixture was warmed on a steam bath for thirty minutes to dryness, and thereafter stirred with water, basified with sodium carbonate and extracted with ethyl acetate. The organic extract was washed with water and saturated sodium chloride solution, dried (anhy. MgSO₄), filtered and concentrated to 8 g oil. This oil was purified by flash chromatography to give 5.5 g oil. A 2.5 g portion was converted to the maleate salt in methanol/ether to give 3.2 g crystals, d 163°-164° C. This solid was recrystallized from methanol/ether to give 2.8 g crystals, d 163°-164° C.

ANALYSIS: Calculated for $C_{21}H_{20}N_4O_4$: 64.28%C, 5.14%H, 14.28%N. Found: 64.14%C, 5.09%H, 14.04%N.

EXAMPLE 65

N-(3-Fluoro-4-pyridinyl)-N-[4-(pyrrolidin-1-yl)-2-butynyl]-1H-indol-1-amine

To 100 ml of p-dioxane were added N-(3-fluoro-4-pyridinyl)-N-(2-propynyl)-1H-indol-1-amine (3.0 g), pyrrolidine (1.2 g), paraformaldehyde (4 g) and CuCl (0.3 g) and this mixture was heated to 80° C. and stirred for 3 hours. The mixture was then cooled and filtered, and the filtrate was concentrated to yield an oil (5.8 g). This material was eluted with 5% methanol/DCM on a silica gel column via HPLC. The desired fractions were concentrated to yield an oil which solidified on standing (3.3 g). This material was then eluted with DCM on an alumina column. The desired fractions were concentrated to yield a solid (2.2 g), which was recrystallized from hexanes/ether (2:1) to yield a solid (1.5 g), m.p. 76°-78° C.

ANALYSIS: Calculated for $C_{21}H_{21}N_4F$: 72.39%C, 6.09%H, 16.08%N. Found: 71.81%C, 5.99%H, 15.87%N.

EXAMPLE 66

3-Aminoethyl-N-propyl-N-(4-pyridinyl)-1H-indol-1-amine di-2-naphthalene sulfonate The title compound was prepared by reduction of 3-cyanomethyl-N-propyl-N-(4-pyridinyl)-1H-indol-1-amine with Raney nickel catalyst in substantially the same manner as in Example 47, m.p. 240° C. (decomp.).

ANALYSIS: Calculated for $C_{38}H_{38}N_4O_6S_2$: 64.21%C, 5.39%H, 7.88%N. Found: 64.12%C, 5.35%H, 7.73%N.

EXAMPLE 67

5-Benzyloxy-N-propyl-N-(4-pyridinyl)-1H-indol-1-amine maleate

The title compound was prepared from 5-benzyloxy-N-(4-pyridinyl)-1H-indol-1-amine and 1-bromopropane with the aid of potassium-t-butoxide in substantially the same manner as in Example 66, m.p. 116°-118° C.

EXAMPLE 68

N-[1-(Propyl-4-pyridinylamino)-1H-indol-3-yl]methyl-N-2-propynylacetamide maleate A solution of 1-(propyl-4-pyridinylamino)-N-2-propynyl-1H-indole-3-methanamine (8 g) in acetic anhydride (50 ml) was warmed on a steam bath for thirty minutes and thereafter cooled and concentrated. The residue was stirred with water, basified with sodium carbonate and extracted with DCM. The dried (anhy. MgSO4) organic layer was concentrated to an oil (9 g). This oil was eluted through silica with methanol/ethyl acetate (1:9) via flash column chromatography to give 6.4 g of an oil. A 2 g portion was converted to the maleate salt in methanol/ether to give 2.2 g of crystals, m.p. 170°-172° C. (decomp.).

ANALYSIS: Calculated for $C_{26}H_{28}N_4O_5$: 65.53%C, 5.92%H, 11.76%N. Found: 65.42%C, 6.07%H, 11.54%N.

EXAMPLE 69

1-(Propyl-4-pyridinylamino)-1H-indole-3-methanol

To a solution prepared from 6 ml of 1.0M LiAlH4/THF and 10 ml of cold THF was added a solution of N-propyl-N-(4-pyridinyl)-1H-indol-1-amine-3-carboxaldehyde (2.0 g) in 10 ml THF.

After stirring at reflux for two hours, the mixture was cooled, quenched with 10 ml saturated NH4Cl solution, and diluted with 25 ml ethyl acetate. The organic layer was collected, washed with water and dried (saturated NaCl, anhydrous MgSO4).

After filtering, the solution was concentrated to a brown oil (2 g), which was eluted on a silica gel column with 5% methanol/DCM via HPLC. The desired fractions were combined and concentrated to a solid (1.3 g), m.p. 36°-38° C.

EXAMPLE 70

1-(Propyl-4-pyridinylamino)-1H-indol-3-ylmethyl acetate hydrochloride

A solution of 1-(propyl-4-pyridinylamino)-1H-indole-3-methanol (2 g) in acetic anhydride (50 ml) was warmed on a steam bath for thirty minutes and thereafter cooled and concentrated. The residue was stirred with water, basified with sodium carbonate and extracted with DCM. The dried (anhy. MgSO4) organic layer was concentrated to an oil and eluted through silica with ethyl acetate to give 2.3 g solid, m.p. 78°-80° C. This was converted to the hydrochloride salt in methanol/ether to give 2.2 g crystals, m.p. 170°-172° C. (decomp.).

ANALYSIS: Calculated for $C_{19}H_{22}ClN_3O_2$: 63.41%C, 6.16%H, 11.68%N. Found: 63.35%C, 6.49%H, 11.66%N.

We claim:

1. A method of preparing a compound of the formula,

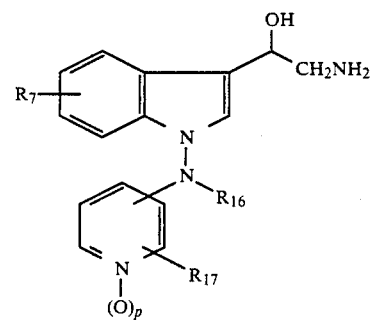

where p is 0 or 1; $R_7$ is hydrogen, halogen, loweralkyl, loweralkoxy, arylloweralkoxy, nitro, formyl, loweralkylthio or loweralkoxycarbonylloweralkylthio; $R_{16}$ is loweralkyl, loweralkoxycarbonyl, alkanoyl, alkenoyl, alkynoyl, arylloweralkanoyl or aroyl; and $R_{17}$ is hydrogen, nitro, halogen or loweralkyl; which comprises reacting a compound of the formula,

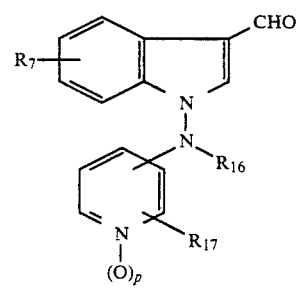

with a compound of the formula,

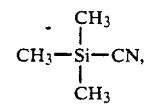

to obtain a compound of the formula,

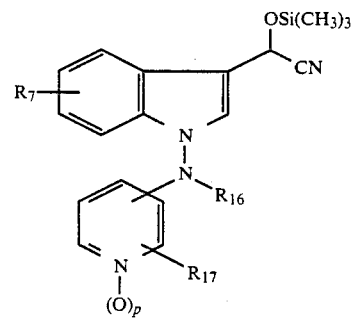

and thereafter reducing the above product with LiAlH4 to obtain said compound.

* * * * *